United States Patent
Wildman et al.

(10) Patent No.: US 10,068,461 B2
(45) Date of Patent: Sep. 4, 2018

(54) REAL-TIME PATIENT EXPERIENCE MONITORING SYSTEM

(71) Applicant: Hill-Rom Services, Inc., Batesville, IN (US)

(72) Inventors: Timothy D. Wildman, Metamora, IN (US); Teresa Brasac, Miami Shores, FL (US); Patrick D. Harrison, Fort Lauderdale, FL (US)

(73) Assignee: Hill-Rom Services, Inc., Batesville, IN (US)

( * ) Notice: Subject to any disclaimer, the term of this patent is extended or adjusted under 35 U.S.C. 154(b) by 15 days.

(21) Appl. No.: 15/461,527

(22) Filed: Mar. 17, 2017

(65) Prior Publication Data

US 2017/0287316 A1 Oct. 5, 2017

Related U.S. Application Data

(60) Provisional application No. 62/318,270, filed on Apr. 5, 2016, provisional application No. 62/409,520, filed on Oct. 18, 2016.

(51) Int. Cl.
| | |
|---|---|
| *G08B 25/12* | (2006.01) |
| *G08B 25/10* | (2006.01) |
| *G06Q 10/08* | (2012.01) |
| *G16H 40/20* | (2018.01) |
| *G06Q 50/22* | (2018.01) |

(52) U.S. Cl.
CPC ........... *G08B 25/12* (2013.01); *G06Q 10/087* (2013.01); *G08B 25/10* (2013.01); *G16H 40/20* (2018.01); *G06Q 50/22* (2013.01)

(58) Field of Classification Search
CPC ................................. G08B 25/10; G08B 25/12

USPC ..................................................... 340/286.07
See application file for complete search history.

(56) References Cited

U.S. PATENT DOCUMENTS

| | | |
|---|---|---|
| 6,317,700 B1 | 11/2001 | Bagne |
| 7,319,386 B2 | 1/2008 | Collins, Jr. et al. |
| 7,552,063 B1 | 6/2009 | McEachern |
| 7,786,874 B2 * | 8/2010 | Rodgers ................ A61B 5/1113 |
| | | 340/573.1 |
| 7,979,286 B2 | 7/2011 | Manning et al. |
| 8,046,625 B2 | 10/2011 | Ferguson et al. |
| 8,169,304 B2 | 5/2012 | Schuman, Sr. et al. |
| 8,384,526 B2 | 2/2013 | Schuman, Sr. et al. |
| 8,452,610 B2 | 5/2013 | Lipner et al. |
| 8,489,414 B2 | 7/2013 | McEachern |
| 8,504,386 B2 | 8/2013 | Manning et al. |
| 8,577,716 B2 | 11/2013 | Bernick et al. |
| 8,577,719 B2 | 11/2013 | Bainbridge et al. |
| 8,583,450 B2 | 11/2013 | Baker et al. |
| 8,598,995 B2 | 12/2013 | Schuman et al. |

(Continued)

FOREIGN PATENT DOCUMENTS

WO 2015148225 A2 10/2015

OTHER PUBLICATIONS

European Search Report dated Jul. 31, 2017.

*Primary Examiner* — Hirdepal Singh
(74) *Attorney, Agent, or Firm* — Barnes & Thornburg LLP

(57) ABSTRACT

A system is provided that monitors information from locating equipment and nurse call equipment and that provides notifications to caregivers so that patient care processes are maintained or modified to ensure high levels of patient satisfaction or patient safety.

19 Claims, 22 Drawing Sheets

(56) References Cited

U.S. PATENT DOCUMENTS

| | | | |
|---|---|---|---|
| 8,779,924 B2 | 7/2014 | Pesot et al. | |
| 9,286,441 B2 | 3/2016 | Zerhausen et al. | |
| 2007/0288263 A1* | 12/2007 | Rodgers | A61B 5/0002 705/2 |
| 2009/0313046 A1 | 12/2009 | Badgett et al. | |
| 2010/0052917 A1* | 3/2010 | Sullivan | A61B 5/6892 340/573.4 |
| 2010/0079276 A1* | 4/2010 | Collins, Jr. | A61B 5/1115 340/539.12 |
| 2012/0316892 A1 | 12/2012 | Huster et al. | |
| 2014/0266642 A1* | 9/2014 | Girardeau | G08B 25/10 340/286.07 |
| 2016/0055299 A1 | 2/2016 | Yarnell | |
| 2016/0296143 A1* | 10/2016 | Hayes | A61B 5/1115 |
| 2017/0186301 A1* | 6/2017 | Vaddepally | H04W 4/023 |

* cited by examiner

Dashboard/Scorecard — 150

| Performance Indicators | | |
|---|---|---|
| | Index | Trend | Previous Shift |
| Patient Satisfaction | 80% | ▭ ▭ ▨ ▨ | 62% |
| Pain Management | 95% | | 85% |
| Patient Safety | 20% | | 65% |
|     Bed Exit | 10% | | 30% |
|     Bed Service | 0% | | 0% |
|     Q2 Turn | 10% | | 15% |
|     Vitals Doc | 95% | | 98% |
| Hand Hygiene | 40% | | 60% |

| | Count | Trend | Calls/Patient/Shift | Trend |
|---|---|---|---|---|
| Patients | 30 | ▭ ▭ ▨ ▨ | 1.5 | ▭ ▭ ▨ ▨ |
| Leader Rounding | 20% | ⌒⌒ | | |

*FIG. 6*

| Call Types | Call Volume | | Response Time | |
|---|---|---|---|---|
| | Count | Trend | Average | Trend |
| Pain Calls | 4 | | 5.5 | |
| Potty Calls | 6 | | 2.5 | |
| Normal Calls | 35 | | 3.5 | |
| All Patient Calls | 45 | | 3.4 | |

*FIG. 7*

| | Staffing | | | Time Spent with Patient | | | |
|---|---|---|---|---|---|---|---|
| | Count | Ratio | Trend | Visits | Time | Average | Avg Trend |
| RN | 5 | 6 | | 10 | 3.3 | 0.3 | |
| PCT | 10 | 3 | | 40 | 13.8 | 0.3 | |
| DR | 2 | 15 | | 4 | 9.3 | 2.3 | |
| Other | 4 | 7.5 | | 30 | 1.6 | 0.1 | |
| Total | 21 | 1.5 | | 84 | 28.0 | 0.3 | |

*FIG. 8*

| FILTER | MEASURE | MEASURE TYPE | CURRENT WEEK | PREVIOUS WEEK | % CHG | 13 WEEK AVG | CURRENT BENCHMARK COMPARISON |
|---|---|---|---|---|---|---|---|
| UNIT TYPE | TOTAL CALLS (OVERALL) | # OF CALLS | 400 | 500 | -25% | 425 | 350 |
| CENSUS | RESPONSE TIME | # OF CALLS | 12 | 14 | -17% | 15 | 16 |
| RESPONSE TIME | | % OF CALLS | 3% | 4% | | | -17% |
| CALL TYPE | PAIN CALLS | # OF CALLS | 12 | 14 | -17% | 15 | 16 |
| | | % OF CALLS | 3% | 4% | | | -17% |
| DATE RANGE | RESPONSE TIME TO PAIN CALLS | # OF CALLS | 12 | 14 | -17% | 15 | 16 |
| HOUR RANGE | | % OF CALLS | 3% | 4% | | | -17% |
| | AVG STAFF ENCOUNTERS (PREV 24HRS) | # OF PT ENCOUNTERS | 1200 | 1500 | -25% | 15 | 16 |
| ROLE | AVG TIME SPENT PER PT VISIT | AVG PT VISIT TIME | 2:25 | 3:30 | | | |
| SHIFT | ROUNDING COMPLIANCE | OPPORTUNITIES | 12 | 14 | -17% | 15 | 16 |
| VIEW | | ROUNDING RATE | 3% | | | | -17% |
| CHART | | | | | | | |
| TABLE | | | | | | | |

*FIG. 11*

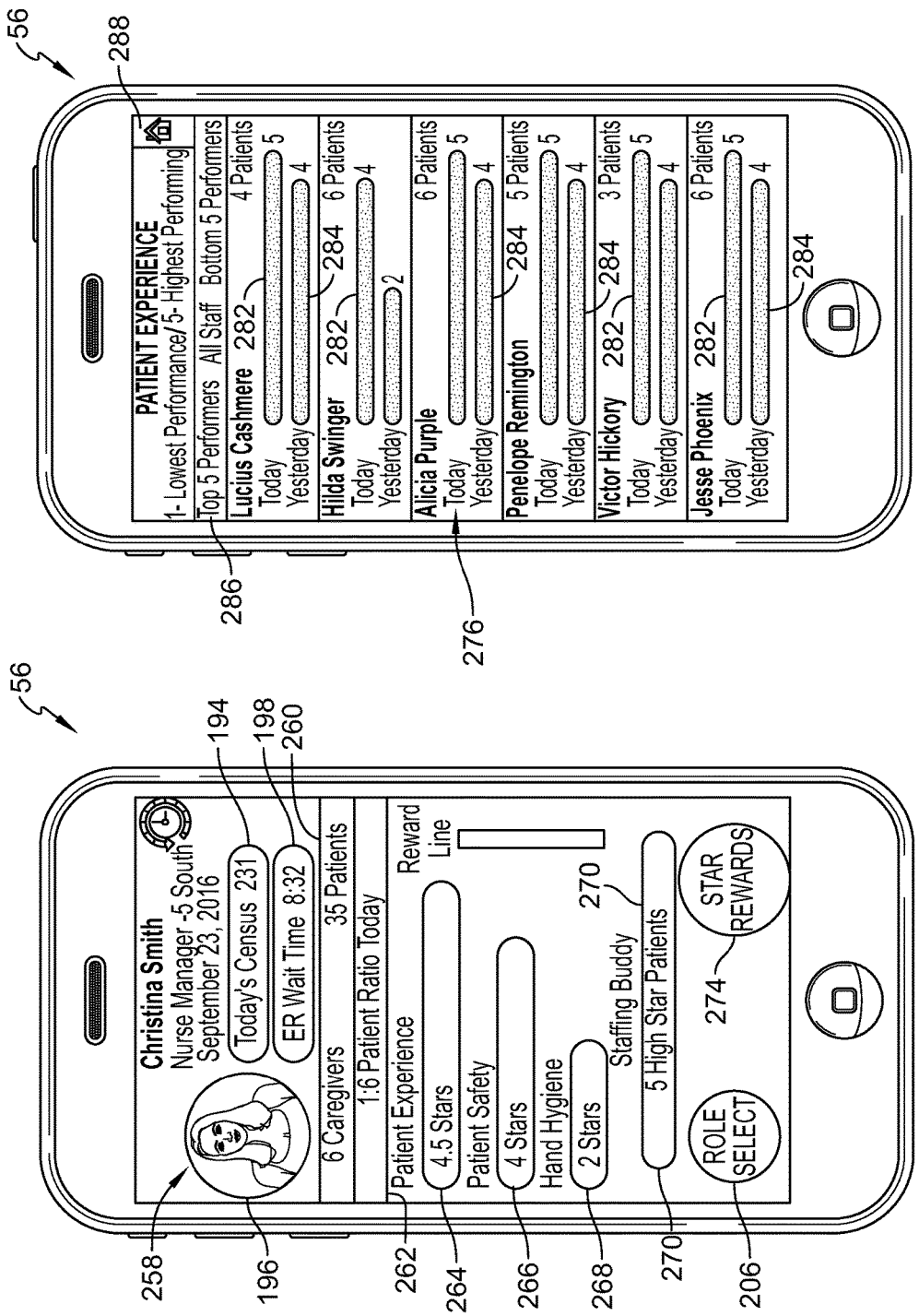

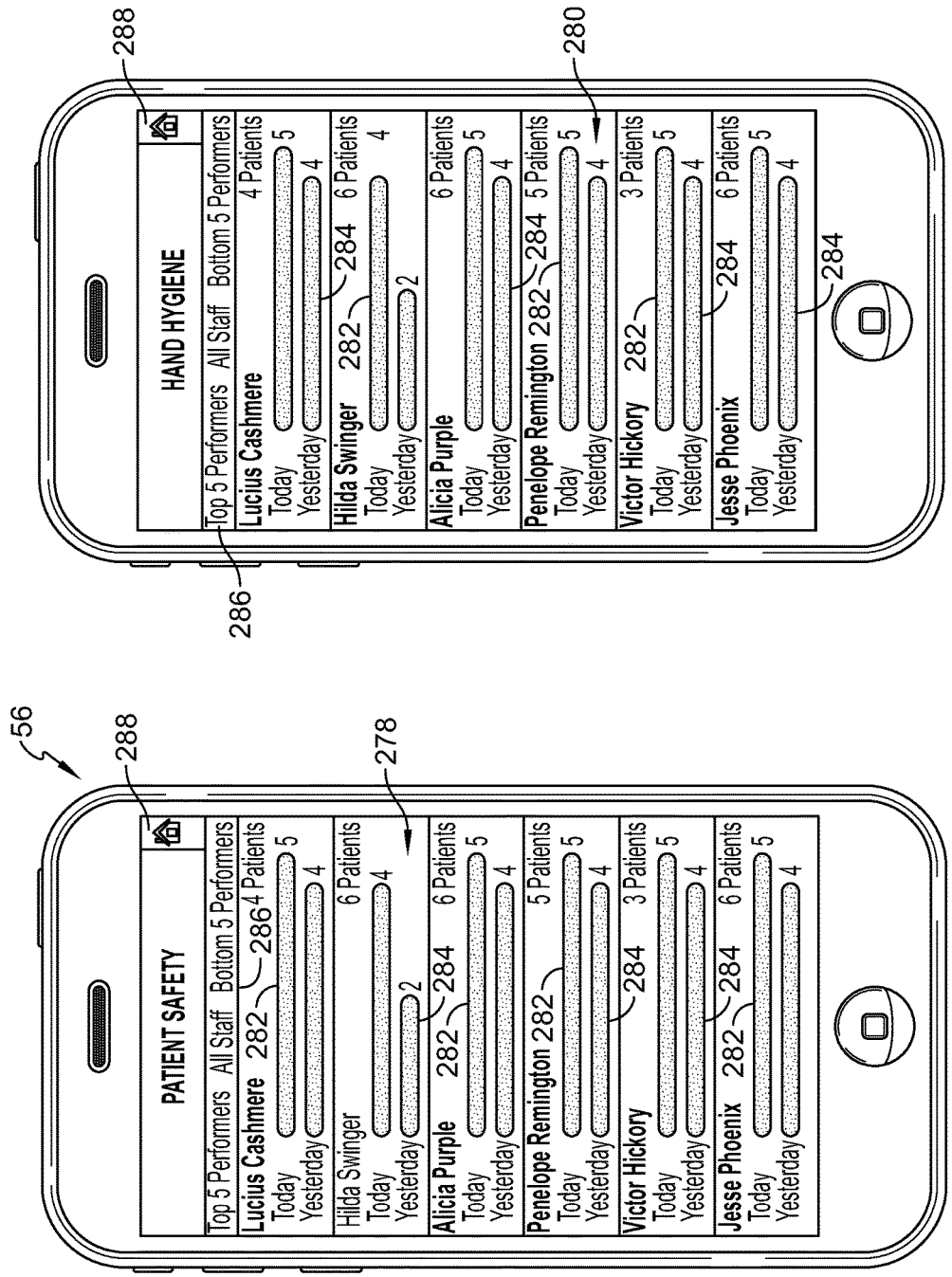

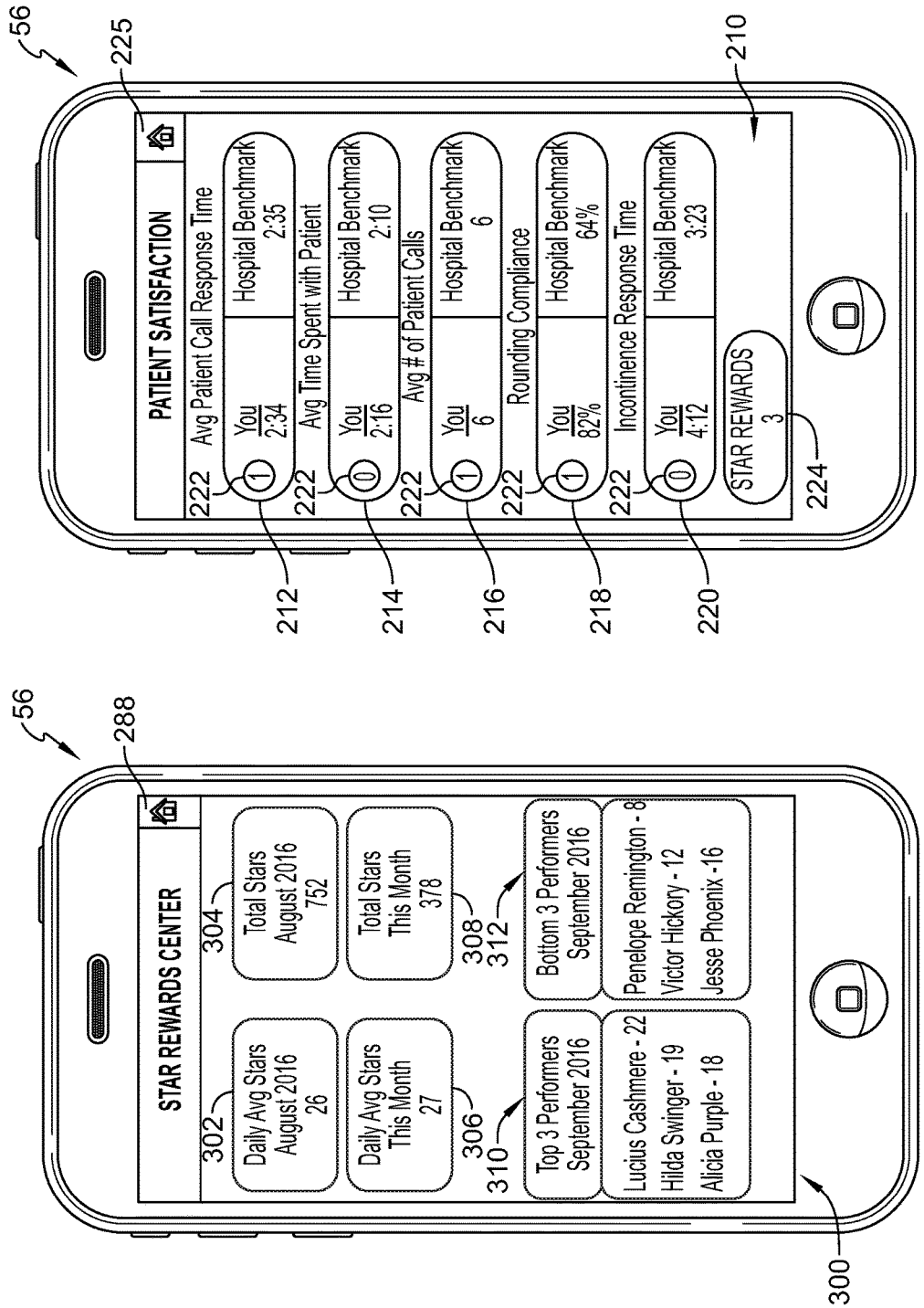

REAL-TIME PATIENT EXPERIENCE MONITORING SYSTEM

The present application claims the benefit, under 35 U.S.C. § 119(e), of U.S. Provisional Application No. 62/318,270, which was filed Apr. 5, 2016, and U.S. Provisional Application No. 62/409,520, which was filed Oct. 18, 2016, each of which is hereby incorporated by reference herein in its entirety.

BACKGROUND

The present disclosure relates to healthcare information systems and particularly, to healthcare information systems having nurse call systems networked with locating systems. More particularly, the present disclosure relates to a real-time patient experience monitoring system of the healthcare information system.

After a patient's stay at a healthcare facility, the patient oftentimes fills out a patient satisfaction survey. For example, the Hospital Consumer Assessment of Healthcare Providers and Systems (HCAHPS) survey has been in use since about 2006 for such purposes. The HCAHPS survey created a national standard throughout the United States for collecting and reporting patient satisfaction information that enables comparisons to be made across participating hospitals to support consumer choice. Almost all hospitals participate because failure to participate impacts Medicare reimbursement. It will be appreciated, therefore, that hospitals desire to have a high HCAHPS score which is indicative of high patient satisfaction with the care received by the patients using the services of the particular hospital. Accordingly, hospitals would welcome a system that informs hospital staff, such as caregivers, of factors that may affect patient satisfaction while the patient is still in the hospital so that corrective measures can be taken, thereby to increase the hospital's HCAHPS scores from patients.

SUMMARY

An apparatus, system, or method may comprise one or more of the features recited in the appended claims and/or the following features which, alone or in any combination, may comprise patentable subject matter:

According to the present disclosure, a system may include locating equipment to track the whereabouts of caregivers in a healthcare facility and nurse call equipment to receive nurse call requests from patients located in patient rooms of the healthcare facility. The nurse call equipment may include at least one nurse call computer that may keep track of an amount of time it takes caregivers to respond to each nurse call and that may keep track of how long at least one caregiver may be present in each patient room based on information received by the nurse call computer from the locating equipment. The system may further include a patient experience module that may receive information from the nurse call equipment regarding types of nurse calls placed by the patients. The types of nurse calls may include a first call type and a second call type. The patient experience module may compare response times for each first call type to a first response time threshold and may compare response times for each second call type to a second response time threshold. The first response time threshold may be a different amount of time than the second time threshold. The patient experience module may initiate an alert to provide a notification that the first response time threshold or the second response time threshold has been exceed for one or more of the first call types or the second call types, respectively.

In some embodiments, the first call type may be a pain call or a potty call and the second call type may be a normal call. The first response time threshold for the pain or potty call may be less than the second response time threshold for the normal call. In some embodiments, the call types may include three call types, such as pain calls, potty calls, and normal calls. In some embodiments, the call types may include more than three call types.

In some embodiments, the information regarding the types of nurse calls placed by the patients may be entered manually by a caregiver into a master nurse station computer of the nurse call equipment based on information that may be communicated to the caregiver verbally by the patients. Alternatively or additionally, the information regarding the types of nurse calls placed by the patients may be determined based on selections that may be made by the patients on nurse call input devices of the nurse call equipment.

The nurse call input devices may comprise handheld pillow speaker units that may have a plurality of nurse call buttons, for example. Each nurse call button of the handheld pillow speaker units may correspond to a call type that may be different than each of the other nurse call buttons of the handheld pillow speaker units. Alternatively or additionally, the nurse call input devices may comprise a plurality of nurse call buttons that may be provided on hospital beds located in the patient rooms. Each nurse call button of the hospital beds may correspond to a call type that is different than each of the other nurse call buttons of the patient beds.

In various embodiments, the notification may include at least one, at least two, at least three or all four of the following: (1) a message appearing on a wireless communication device carried by at least one caregiver (2) a message appearing on a status board display located in a caregiver work area, (3) a message appearing on a master nurse station computer of the nurse call system, or (4) illumination of at least one light of an indicator assembly located adjacent a door of at least one of the patient rooms.

In some embodiments, at least one of the first response time threshold or the second response time threshold may be based on historical data from patient satisfaction surveys. Optionally, the first response time threshold and the second response time threshold may be based on historical data from patient satisfaction surveys.

According to another aspect of the present disclosure, a system may include locating equipment to track the whereabouts of caregivers in a healthcare facility and nurse call equipment to receive nurse call requests from patients located in patient rooms of the healthcare facility. The patient rooms may be divided up into at least a first unit of the healthcare facility and a second unit of the healthcare facility. The nurse call equipment may include at least one nurse call computer that may keep track of an amount of time it takes caregivers to respond to each nurse call and that may keep track of how long at least one caregiver is present in each patient room based on information received by the nurse call computer from the locating equipment. The system may also include a patient experience module that may receive information from the nurse call equipment regarding types of nurse calls placed by the patients. The types of nurse calls may include a first call type and a second call type. The patient experience module may compare response times for each first call type to a first response time threshold for the first unit and may compare response times for each second call type to a second response time threshold for the first unit. The first response time threshold may be a different amount of time than the second time threshold. The patient experience module may initiate an alert to provide a notification that the first response time threshold or the second response time threshold may have been exceeded for one or more of the first call types or the second call types of the first unit, respectively. The patient experience module may compare response times for each first call type to a third response time threshold for the second unit and may compare response times for each second call type to a fourth response time threshold for the second unit. The third response time threshold may be a different amount of time than the fourth time threshold. The patient experience module may initiate an alert to provide a notification that the third response time threshold or the fourth response time threshold may have been exceeded for one or more of the first call types or the second call types of the second unit, respectively.

In some embodiments, the first response time threshold may be a different amount of time than the third response time threshold. Alternatively or additionally, the second response time threshold may be a different amount of time than the fourth response time threshold. The first unit may comprise one of a maternity unit, a pediatrics unit, an intensive care unit, or a med/surg unit, for example, and the second unit may comprise a different one of the maternity unit, the pediatrics unit, the intensive care unit, or the med/surg unit than the first unit.

According to a further aspect of the present disclosure, a system may include locating equipment to track the whereabouts of caregivers in a healthcare facility and nurse call equipment to receive nurse call requests from patients located in patient rooms of the healthcare facility. The nurse call equipment may include at least one nurse call computer that keeps track of the following key performance parameters: (1) a number of calls, (2) an amount of time it takes caregivers to respond to each nurse call, (3) a number of times at least one caregiver enters a patient room of a respective patient, and (4) how long at least one caregiver is present in each patient room. The key performance parameters may be determined by the nurse call computer based on information received from other nurse call equipment and received from the locating equipment. The system may further have a patient experience module that may initiate an alert to provide a notification that any one or more of the key performance parameters may exceed a respective parameter threshold.

In some embodiments, the respective key parameter threshold may be determined based on historical data from patient satisfaction surveys. Optionally, the key performance parameters may further include one or more of the following: (5) a number of patient beds communicatively coupled to the nurse call equipment, (6) a number of patient beds having a bed exit system of the respective patient beds armed, or (7) a rounding compliance index.

According to a further aspect of the present disclosure, a system for providing performance information to a caregiver may be provided. The system may include a data repository and a portable computer in communication with the data repository. The portable computer may be operable to display one or more of the following: average patient call response time, average time spent with one or more patients, average number of patient calls, rounding compliance percentage, incontinence response time, bed safety information, patient deterioration information, safe patient handling information, number of rewards points earned by caregivers, hand washing compliance percentage, patient satisfaction information, a patient needs score, a staff timeline indicating names of caregivers who have visited patient rooms and the duration of the visit, number of patient calls per patient, modified early warning system (MEWS) scores for patients, the number of times a patient has needed assistance, information regarding status of beds of patients, number of patient lifts, or performance threshold achievement information.

Additional features, which alone or in combination with any other feature(s), such as those listed above and those listed in the claims, may comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The detailed description particularly refers to the accompanying figures in which:

FIG. 5 is an example of a first dashboard or scorecard relating to patient experience performance indicators;

FIG. 6 is an example of a second dashboard or scorecard relating to number of calls per patient per shift;

FIG. 7 is an example of a third dashboard or scorecard relating to call volume and response time;

FIG. 8 is an example of a fourth dashboard or scorecard relating to staffing and time spent by caregivers with patients;

FIG. 11 is a screen shot of a scorecard showing week-by-week comparisons of various patient experience statistics;

FIG. 21 is a screen shot of an informational overview screen for a nurse manager as displayed on a smart phone;

FIG. 22 is a screen shot of a second patient experience screen as displayed on a smart phone;

FIG. 23 is a screen shot of a second patient safety screen as displayed on a smart phone;

FIG. 24 is a screen shot of a second hand hygiene screen as displayed on a smart phone;

FIG. 25 is a screen shot of a rewards center screen as displayed on a smart phone;

FIG. 26 is a screen shot of a patient satisfaction screen as displayed on a smart phone;

DETAILED DESCRIPTION

Figure 1:
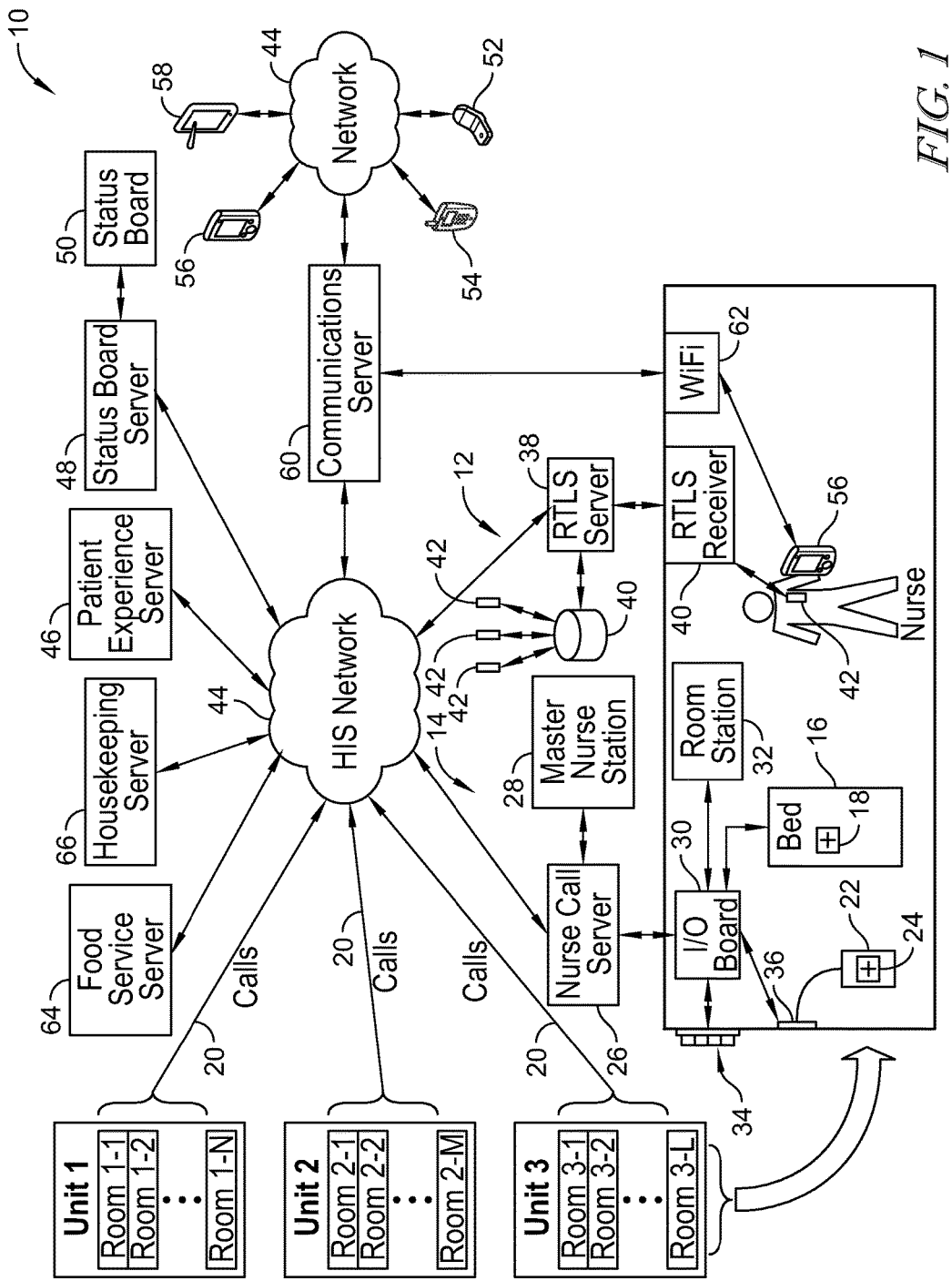
FIG. 1 is a block diagram of a healthcare information system for use in a healthcare facility having patient rooms in various units of the healthcare facility; the healthcare information system including various servers, nurse call equipment, and locating equipment; the nurse call equipment including a nurse call server, a master nurse station coupled to the nurse call server, room stations located in the patient rooms, indicator assemblies located outside the patient rooms and coupled to the room stations via an input/output (I/O) board, and nurse call buttons on a patient bed and/or on a handheld pillow speaker unit; and the locating equipment including locating tags worn by caregivers, real-time locating system (RTLS) receivers located in the patient rooms, and an RTLS server coupled to the RTLS receivers.

According to the present disclosure, a system 10 includes locating equipment 12 to track the whereabouts of caregivers in a healthcare facility and nurse call equipment 14 to receive nurse call requests from patients located in patient rooms of the healthcare facility as shown diagrammatically in FIG. 1. The healthcare facility is divided up into units as also shown diagrammatically in FIG. 1 as unit 1, unit 2, and unit 3. Units 1-3 each have patient rooms which, in the illustrative example, are shown as rooms 1-1 through 1-N for unit 1, rooms 2-1 through 2-M for unit 2, and rooms 3-1 through 3-L for unit 3. Letters N, M and L represent integers corresponding to the overall number of rooms in the corresponding unit 1-3 and the use of different letters is intended to indicate that different units may not necessarily have the same number of rooms.

While healthcare facilities may have any number of units with various unit names and all such facilities are intended to be within the scope of the present disclosure, examples of units of a healthcare facility may include, for example, a maternity unit, a pediatrics unit, an intensive care unit, and a med/surg unit, just to name a few. Each room of each unit has a patient support apparatus, such as a hospital bed 16 as shown in FIG. 1 in the enlarged diagrammatic view of one patient room. In some embodiments, bed 16 has a nurse call button 18 which is pressed by a patient send a nurse call to the nurse call equipment 14 of system 10. Alternatively or additionally, some rooms may have a handheld pillow speaker unit 22 with its own nurse call button 24 as shown diagrammatically in FIG. 1. Nurse calls originating from the various patient rooms of units 1-3 in response to buttons 18, 24 being pressed are represented by arrows 20 in FIG. 1. Buttons 18, 24 and/or handheld pillow speaker unit 22 may be considered part of nurse call equipment 14 in some embodiments.

Nurse call equipment 14 includes a nurse call server 26 and a master nurse station 28 as shown diagrammatically in FIG. 1. It should be appreciated that some healthcare facilities may have two or more servers 26 and two or more master nurse stations. For example, a master nurse station may be provided for each unit of the healthcare facility if desired. In the illustrative example, nurse call equipment 14 also includes, in each room, an input/output (I/O) board 30 that receives nurse call signals from the one or more beds 16 and units 22 in the room. Nurse call equipment 14 also includes at least one room station 32 in each room and at least one indicator assembly 34 (sometimes referred to as a dome light assembly or just a dome light) located in a hallway adjacent to the room. Each I/O board 30 is communicatively coupled to a respective server 26, room station 32, and indicator assembly 34. In the illustrative example, a wall connector 36 is provided for coupling to a cable extending from unit 22 and the connector 36 is coupled to I/O board 30.

I/O board 30 passes any nurse calls 20 made by a patient using button 18 or button 24 to server 26. Information concerning the nurse calls 20 made in the various rooms is displayed on display screens, such as graphical user interfaces (GUI's), of room stations 32 and master nurse station 28. In some embodiments, additional components are included in nurse call equipment 14 such as, for example, bed interface units (BIU's), routers, gateways, cabling, etc. One example of nurse call equipment 14 contemplated by the present disclosure is the NAVICARE® nurse call system available from Hill-Rom Company, Inc. Additional details of suitable nurse call equipment 14 that may be included in system 10 are shown and described in U.S. Pat. Nos. 8,598,995; 8,384,526; 8,169,304; 8,046,625 and 7,319,386; each of which is hereby incorporated by reference herein to the extent not inconsistent with the present disclosure which shall control as to any inconsistencies.

Still referring to FIG. 1, locating equipment 12 includes a real-time locating system (RTLS) server 38, a multitude of RTLS receivers 40 located throughout the healthcare facility, and a multitude of RTLS badges or tags 42 that are worn by caregivers, such as by being clipped to the caregiver's clothing for example. As the caregivers travel throughout the healthcare facility, tags 42 transmit signals to the receivers 40 at the caregiver's location. The signals from tags 42 each include a unique tag identification code or number (ID) that is correlated in a database of server 38 to the identity of the caregiver to which the particular tag 42 has been assigned. Receivers 40 each transmit to server 38 a receiver ID along with the tag ID of any tags 42 within the reception range of the particular receiver 40. The receiver ID is correlated in the database of server 38 to a particular location, such as a room or hallway, of the healthcare facility. Thus, based on the transmissions from the various receivers 40 of receiver ID and tag ID, server 38 determines the location of each of the caregivers having an associated tag 42 within the healthcare facility. Tags 42 may be attached to particular pieces of equipment (e.g., beds, wheelchairs, IV pumps, vital signs monitors, etc.) so that locating equipment 12 is able to track the locations of the equipment in a similar manner, if desired.

It is within the scope of the present disclosure for locating equipment 12 to implement any of a variety of wireless communication technologies to achieve the function of tracking the whereabouts of caregivers in a healthcare facility. Radio frequency (RF) including WiFi (i.e., 802.11) or Bluetooth (BT), infrared (IR), ultrasonic (US), ultra wide band (UWB), and so forth are a few examples of such technologies. In some embodiments, for example, locating units (not shown) mounted throughout the healthcare facility transmit IR signals to tags 42. The IR signals are encoded with a location ID which correlates in the database of server 38 to the location of the locating unit. The tags 42 then transmit the location ID's and tag ID's as an RF signal to receivers 40. Thus, tags 42 in such embodiments have an IR receiver and an RF transmitter. The receivers 40 transmit the location ID's (sent originally via IR) and the tag ID's to server 38 for correlation. Thus, receivers 40 may be more accurately characterized as receiver/transmitters or transceivers in some embodiments since they both transmit and receive. Such a system that uses IR and RF technology for locating is marketed, for example, by Centrak Inc. of Newtown, Pa.

Nurse call equipment 14 and locating equipment 12 are communicatively coupled to one another by a healthcare information system (HIS) network 44 which is illustrated diagrammatically in FIG. 1 but which is intended to represent all of the infrastructure of a healthcare facility, such as gateways, routers, cabling, network servers, and the like, used to interconnect computer devices including various servers, such as servers 26, 38, in a healthcare facility. In this regard, nurse call server 26 of nurse call equipment 14 receives information from RTLS server 38 of locating equipment 12 regarding the location of various caregivers having tags 42, as they travel throughout the healthcare facility.

According to this disclosure, each time a patient places a nurse call 20, nurse call server 26 keeps track of the amount of time that elapses subsequent to the respective nurse call 20 being placed. Thus, each nurse call 20 has a timer associated therewith which is implemented in nurse call software executed by server 26. When a caregiver wearing one of tags 42 enters a particular room having an outstanding nurse call 20, nurse call server 26 stops the timer of the nurse call 20 for that particular room, either substantially in real time upon entry of the caregiver into the room or after a threshold amount of the caregiver's presence in the room, such as one to five minutes, for example. As such, nurse call server 26 is able to keep track of nurse call response times for each nurse call 20. Server 26 also has data concerning the overall total number of nurse calls at any given time. Data from server 38 also indicates how long each caregiver having a respective tag 42 is present in each patient room.

According to this disclosure, a patient experience server 46 is coupled to network 44. Patient experience server 46 includes software, sometimes referred to herein as a patient experience module, which monitors and analyzes the data associated with servers 26, 38. In some embodiments, the patient experience module is included in server 26 and/or server 38 in which case server 46 may be omitted, if desired. Thus, the patient experience module receives data concerning call volume (i.e., number of nurse calls 20 at any given time), nurse call timer information at any given time, and response times associated with each of the nurse calls 20 that are placed. In some embodiments, the patient experience module receives information from nurse call equipment 14 regarding different types of nurse calls 20 that are placed by the patients. The types of nurse calls 20 include, for example, pain calls, potty calls, and normal calls.

The patient experience module has stored therein, various response time thresholds. The response time thresholds represent an amount of time that, based on historical patient experience survey information, corresponds to a highly rated patient experience. For example, a response time to a pain call or potty call on the order of two or three minutes may be acceptable to most patients, whereas a response time to normal calls of five to ten minutes may be acceptable to most patients, just to give an arbitrary example. In another arbitrary example, the patient experience module is configured so that a response to a potty call (sometimes referred to as a "bath request") is acceptable if less than two minutes, a response to a pain call is acceptable if less than six minutes, and response to a normal call is acceptable if less than three minutes. The patient experience module compares the response times for each of the call types to the corresponding response time threshold and, in appropriate circumstances in which the response time threshold has been exceeded for a particular nurse call 20, the patient experience module initiates an alert to provide a notification that the particular response time threshold has been exceeded for the particular nurse call 20.

Server 26 also provides to the patient experience module information concerning which unit (e.g., units 1-3) each of the calls originated. According to this disclosure, response time thresholds for the same type of call vary by unit. For example, a response time to a normal call of up to ten minutes may be acceptable in a maternity unit whereas a response time to a normal call that exceeds five minutes may be unacceptable (i.e., too long) in a med/surg unit. Thus, the response time threshold for a normal call may be ten minutes for a maternity unit and may be only five minutes for a med/surg unit, just to give an arbitrary example. The longer response time threshold for a maternity unit may be explainable by the fact that caregivers tend to spend more time with new and expectant mothers during patient room visits in a maternity unit. Thus, the longer in-room attention to patients by caregivers in maternity units translates to a willingness by the patients to wait longer to have normal calls responded to in the future. Similar response time variability from unit-to-unit is also contemplated for other types of calls, such as pain calls and potty calls.

In connection with segregating nurse calls 20 into different call types, it is contemplated that, in some instances, this is done manually by a caregiver at master nurse station 28. For example, the nurse at the master station 28 who sees a new incoming nurse call 20 on the GUI screen of station 28 may open a voice communication channel to the patient and ask the patient to provide further information as to why the nurse call 20 was made. Based on the patient's response (e.g., "I need to go to the bathroom" or "I need pain medication" or "I need more water"), the nurse designates the call type as a potty call, a pain call or a normal call by making appropriate entries or selections on the GUI of station 28. Alternatively or additionally, the patient is able to designate the type of nurse call 20 being made. For example, some handheld pillow speaker units 22 have more than one button 24, such as having a pain call button, a potty call button, and a normal call button. This disclosure contemplates that beds 16 may be similarly equipped with multiple call type buttons.

In some scenarios contemplated by this disclosure, patient's have their own tablets or smart phones on which communication software is installed for interfacing with system 10 via network 44. Alternatively or additionally, a healthcare facility may provide the patient with a tablet or other digital device for use during their stay at the facility. Various call type icons are displayed on the GUI of the patient's personal digital device in connection with the communication software. Selection of a call type icon on the patient's GUI results in a nurse call 20 being sent to server 26 with information concerning the call type. In this regard, see, for example, U.S. Patent Application Publication No. 2016/0055299 which is hereby incorporated by reference herein to the extent not inconsistent with the present disclosure which shall control as to any inconsistencies. Beds 16 with patient GUI's for placing specific call types are also within the scope of this disclosure. See, for example, U.S. Pat. No. 9,286,441 which is hereby incorporated by reference herein to the extent not inconsistent with the present disclosure which shall control as to any inconsistencies.

It is also contemplated by this disclosure that a variety of different types of alerts and notifications can be initiated by the patient experience module. For example, when a nurse call 20 is placed by a patient in a particular room, one of the lights of indicator assembly 34 associated with the room becomes illuminated in a first state, such as for example, a non-flashing amber or yellow light. In some embodiments, if the nurse call 20 is not answered by a caregiver visiting the patient room within a first threshold amount of time, the patient experience module signals the particular indicator assembly 34 via server 26 and I/O board 30 to cause the yellow light to flash on and off. If the nurse call 20 is not answered by a caregiver visiting the patient room within a second threshold amount of time, the patient experience module signals the indicator assembly 34 via server 26 and I/O board 30 to illuminate a red light and to turn off the flashing yellow light. In some embodiments, if a caregiver at master nurse station 28 opens up a communication channel to speak with the patient placing the nurse call, then server 26 signals indicator assembly 34 via I/O board 30 to illuminate a green light. Thus, the lights of indicator assemblies 34 serve as one type of alert or notification to caregivers as to the status of the associated nurse calls 20 and whether nurse calls 20 are being answered by caregivers with visits to the patient rooms within acceptable time thresholds.

Alerts and notifications initiated by the patient experience module include messages on display screens of various computer devices in some embodiments. For example, the patient experience module may send a signal to server 26 to cause a message or icon to be displayed on the GUI of master nurse station 28 in connection with one or more nurse calls 20 to indicate that a response time threshold has been exceeded. In some embodiments, system 10 includes a status board server 48 which communicates with servers 26, 38, 46 via network 44. One or more status boards 50 are coupled to server 48. The patient experience module may send a signal to server 48 to cause a message or icon to be displayed on the status board 50 in connection with one or more nurse calls 20 to indicate that a response time threshold has been exceeded. Status board 50 typically includes a display screen that is much larger than a display screen of a regular computer or master nurse station 28. The status board 50 is usually mounted in an area that is highly trafficked by caregivers so as to be readily visible by caregivers during their shifts. For additional details of a suitable status board 50, see U.S. Pat. No. 8,779,924 which is hereby incorporated by reference herein to the extent not inconsistent with the present disclosure which shall control as to any inconsistencies.

Further according to this disclosure, computer devices that receive alerts and notifications initiated by the patient experience module include wireless communication devices carried by caregivers. As shown in FIG. 1, such wireless communication devices include, for example, telephone handsets 52, pagers 54, smart phones 56, and tablet computers 58. Each of these wireless devices 52, 54, 56, 58 have a display screen on which the message and/or alert is displayed. One or more communications servers 60 are provided in system 10 in the illustrative example to facilitate the communication of such alerts or notifications from one or more of servers 26, 38, 46 to devices 52, 54, 56, 58. One or more of servers 60 may be a voice over Internet Protocol (VoIP) server in some embodiments. As shown in FIG. 1, system 10 includes other communication infrastructure, such as wireless access points 62 that are communicatively coupled to server 60 and that are mounted throughout the healthcare facility.

Figure 2:
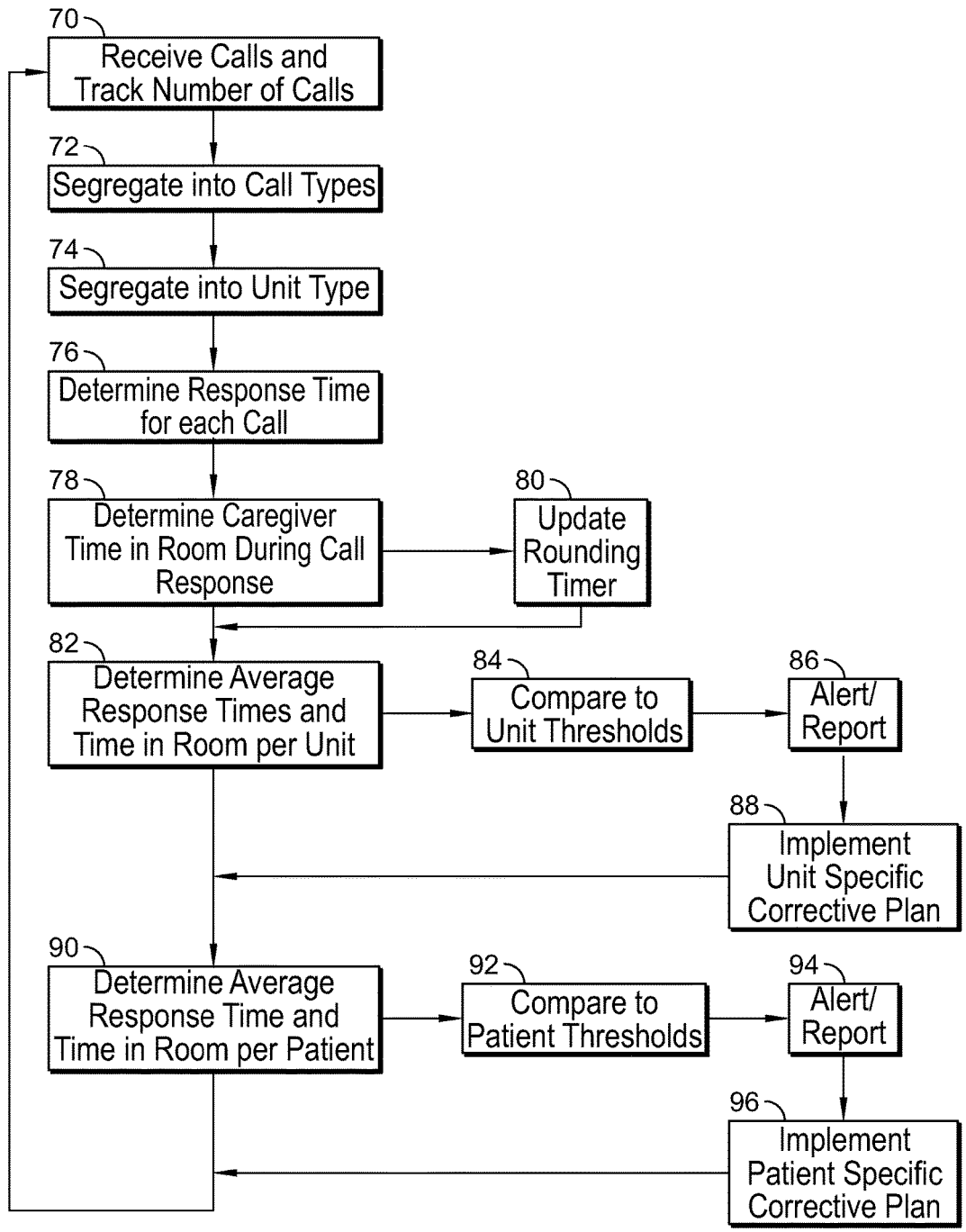
FIG. 2 is a flow chart of a process implemented by one or more of the servers, such as a patient experience server and the nurse call server of FIG. 1, to provide alerts regarding performance parameters that affect patient satisfaction.

Referring now to FIG. 2, a flow chart is provided and is illustrative of the functionality of the patient experience module which, as mentioned above, is embodied as software stored in memory of one or more of servers 26, 38, 46 and executed by the respective processors of the servers 26, 38, 46. As indicated at block 70, the patient experience module receives nurse calls 20 and tracks the overall number of calls received. As indicated at block 72, the patient experience module segregates the nurse calls 20 into the various call types. As indicated at block 74, the patient experience module also segregates the nurse calls 20 by unit type. As caregivers respond to the various nurse calls 20 in the various units, the patient experience module determines the response time for each call (i.e., how long it took before a caregiver attended to the nurse call 20) as indicated at block 76.

Still referring to FIG. 2, at block 78 the patient experience module determines an amount of time that a caregiver spends in a patient's room during a response to a nurse call 20. If the caregiver spends a sufficient amount of time in the patient's room (e.g., more than a threshold amount), then the patient experience module updates a rounding time for the particular patient or sends a message to one or more of servers 26, 38, 48 to update the rounding timer as indicated at block 80. At block 82, the patient experience module determines average response times and the average time that caregivers spent in each of the patient rooms within each unit when responding to nurse calls 20. In connection with block 82, the averages can be taken at time intervals that are selected by a user of the patient experience module. For examples, the patient experience module can be programmed to calculate the averages hourly, by shift, daily, etc.

At block 84, the patient experience module compares the averages to the thresholds established for each of the respective units. After making the per-unit comparison, the patient experience module generates an alert (and/or notification) and a report to indicate the results of the per-unit comparison as indicated at block 86. If the per-unit comparison indicates that one or more thresholds are exceeded or not met, such as the average time to respond to nurse calls being too long for a particular unit or the time in the patients' rooms when responding being too small for a particular unit, then a unit specific corrective plan is implemented as indicated at block 88. In this regard, the patient experience module may provide recommended corrective actions in an electronic report that is sent to one or more caregivers via e-mail, for example.

At block 90, the patient experience module determines on a per-patient basis, the average response times and the average time that caregivers spent in each of the patient rooms when responding to nurse calls 20. In connection with block 90, the averages can be taken at time intervals that are selected by a user of the patient experience module. For example, the patient experience module can be programmed to calculate the averages hourly, by shift, daily, etc.

At block 92, the patient experience module compares the averages to the thresholds established for each of the respective patients or rooms. After making the per-patient comparison, the patient experience module generates an alert (and/or notification) and a report to indicate the results of the per-patient comparison as indicated at block 94. If the per-patient comparison indicates that thresholds are exceeded or not met, such as the average time to respond to nurse calls being too long for a particular patient or the time in the patients' rooms when responding being too small for a particular patient, then a patient specific corrective plan is implemented as indicated at block 96. In this regard, the patient experience module may provide recommended corrective actions in an electronic report that is sent to one or more caregivers via e-mail, for example.

In connection with call type segregation of block 72, it is within the scope of this disclosure for there to be call types in addition to or in lieu of the pain calls, potty calls, and normal calls mentioned above. Just to give a couple additional examples, system 10 may have a foot service server 64 and a housekeeping server 66 as shown diagrammatically in FIG. 1. System 10 may have one or more additional computer devices (not shown) coupled to server 64 and/or server 66. Server 64 keeps track of food requests (e.g., breakfast, lunch and dinner orders) made by the various patients in the rooms of the various units. The amount of time it takes to deliver food to each of the patients is tracked by server 64. The food delivery time can be compared to thresholds and alerts or notifications can be sent to caregivers, such as food service personnel, in the same manner as described above for other types of alerts and notifications.

In some embodiments, system generated calls by server 64 are established in response to delivery of food trays to patients. For example, based on patient experience survey data, it may be determined that patients expect their food trays and associated food trash items to be picked up and removed from their room within a certain amount of time after the meal is delivered. One hour may be an appropriate time threshold in this regard. Accordingly, in some embodiments, food service workers provide inputs to server 64 regarding the time at which each meal was delivered to a respective patient and then server 64 generates a tray/trash pick-up call one hour later (or whatever time later is determined to provide positive patient experiences).

Housekeeping server 66 keeps track of housekeeping requests such as requests to clean up spills, deliver new bed lines, empty trash cans, and the like. The patient experience module may have response time thresholds stored therein for each of these housekeeping activities. The amount of time it takes to perform the housekeeping activity for each of the patients after a housekeeping call is generated may be tracked by server 66 and/or server 46. The housekeeping call response times can be compared to thresholds and then, alerts or notifications can be sent to caregivers, such as housekeeping personnel, in the same manner as described above for other types of alerts and notifications.

Figure 4:
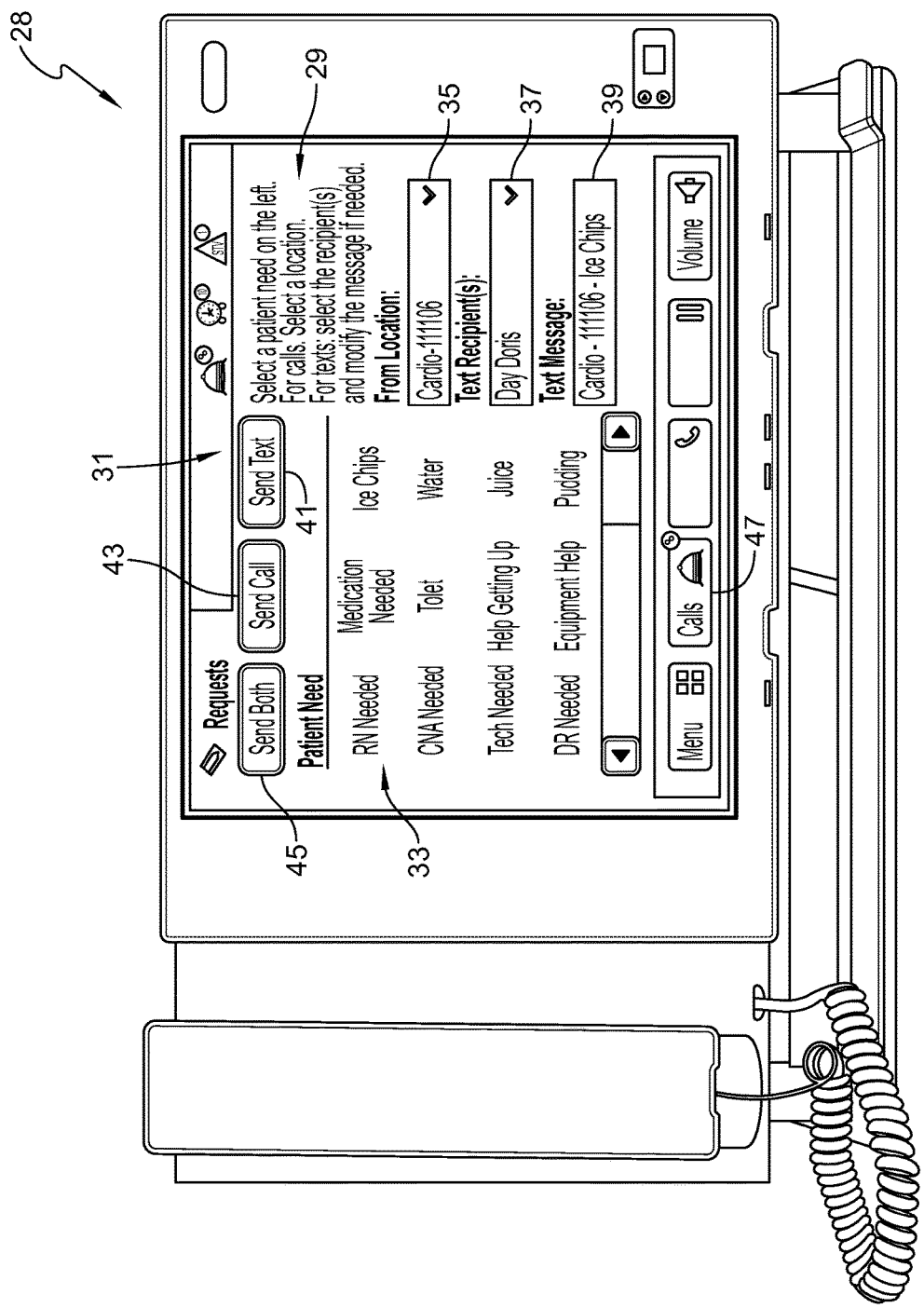
FIG. 4 is a screen shot of a text request screen appearing on the master nurse station of the nurse call equipment of FIG. 1 showing a table of selectable call types and text message windows to the right of the table of selectable call types.

Referring now to FIG. 4, a text request screen 31 is shown on a GUI 29 of master nurse station 28. Screen 31 includes a table 33 with a number of specific call type fields that are selectable by a caregiver to indicate a particular call type. In the illustrative example, the call types within the selectable fields of table 33 are RN Needed, Medication Needed, and Ice Chips in the first row of the table 33; CNA Needed, Toilet, and Water in the second row of the table 33; Tech Needed, Help Getting Up, and Juice in the third row of the table 33; and DR Needed (i.e., doctor needed); Equipment Help, and Pudding in the fourth row of the table 33. Also included on screen 31 are text message windows including a From Location window 35, a Text Recipient(s) window 37, and a Text Message window 39. Window 35 is populated automatically with the room information from which the particular call originated. Window 37 is populated automatically with the name of the primary caregiver assigned to the room from which the call originated. Additional caregivers can be added to window 37 by the caregiver at the master nurse station 28 if desired. Window 39 is populated with the text message to be sent to the caregivers listed in window 37. The text message defaults to the room number from which the call originated plus the call type selected from table 33.

Screen 31 also includes a Send Text button 41, a Send Call button 43, and a Send Both button 45. Selection of button 41 causes the text message appearing in window 39 being sent to the wireless communication device 52, 54, 56, 58 of each of the recipient(s) listed in window 37. Selection of button 43 causes a phone call to be made to the wireless communication device 52, 54, 56 (and device 58 if it has voice communication capability) of each of the recipient(s) listed in window 37. Selection of button 45 causes both a text message and a phone call to be made to the wireless communication device 52, 54, 56, 58 of each of the recipient(s) listed in window 37. A calls button 47 is provided on screen 31 and is selected by the caregiver at master nurse station 28 to return to a screen showing a list of the incoming calls.

According to the present disclosure, the patient experience module of server 46 receives, uses, calculates or analyzes the following types of data:

Entity=patient, staff, Room, Unit, Shift, Facility, Division, Group and Enterprise or any combination thereof;

Interval=immediately, Hour, trending time period (multiple hours) Shift, day, Month, Year, or any combination thereof;

Value=This is the median, mode or mean for the set of values in an interval;

Call Type=All, Normal, all Pain, all Bath, Assistance needed, Water, ice, potty, IV alarming, food tray removal, meds or any combination thereof;

Call Volume=The count of events for a given Entity, Interval and Call Type;

Call Total Response time=the elapse time between when a call is placed until it is canceled for a given Interval and Call Type;

Interval Response times: time placed to time answered at station, time answered at station to wait list;

Patient Encounters=The count of times individuals enter a room for a given Interval;

Direct Patient Care=The total amount of time spent with a patient for a given Interval;

Bed Engagement=The number of beds 16 connected to the nurse call equipment 14 for a given Entity and Interval;

Bed Safety=The number of beds 16 with bed exit engaged for a given Entity and Interval; and Limit=This is the maximum or minimum limit of a threshold Value that should not be crossed. This value may change based on Staffing Ratios, Intervals, etc.

In some embodiments, the patient experience module determines the following Key Performance Indexes (KPIs):

Call Volume Index—A score calculated based on the Call Volume and an associated Limit;

Response Time Index—A score calculated based on the Total Response Time and the associated Limit;

Patient Encounter Index—A score calculated based on the Patient Encounters and the associated Limit;

Direct Patient Care Index—A score calculated based on the Direct Patient Care value and the associated Limit;

Bed Engagement Index—A score calculated based on the Bed Engagement value and the associated Limit Bed Safety Index—A score calculated based on Bed Safety value and the associated Limit; and Rounding Index—A score calculated based on a compliance rate to staff rounding per patient and an established Limit.

In some embodiments, KPIs may comprise any combination of the above-listed indexes. It is contemplated by this disclosure that the above-described indexes may be normalized into a common numerical range such as 0-10 or 0-100. In this regard, an example is given below in which Call Volume Index is normalized into a range of 0-10. For example, the Call Volume Index is modified by converting the Limit to a score where 0=is the poorest rating and 10=best possible rating. This measure may be as simple as not to exceed 400 calls per Interval or a ratio of Call Volume per number of Patients per Interval e.g. 5 calls/patient/Interval a per patient/time measure for this, or we can calculate based on census). With the foregoing in mind, the example is given as follows:

Call Volume Limit using 400 calls as the limit:
Index of 10=50% below the Limit=200
Index of 5=Limit=400
Index of 0=50% above the limit=600
Values between 0 and 10 are equal segments
Index 10=200—Great (green)
Index 9=240
Index 8=280
Index 7=320
Index 6=360
Index 5=400—Average (Yellow)
Index 4=440
Index 3=480
Index 2=520
Index 1=560
Index 0=600—Poor (Red)

The limit is set for each Index and its associated Entity and Interval. Thus, each of the KPI's may be normalized in a manner similar to that just described, if desired. The system monitors the trending of the KPIs and provides pro-active notifications when limits are about to be exceeded through visual and auditable signals.

One advantage of the above-described scoring methodology is that it normalizes all elements independent of the values, entities, or intervals, thus making it a comparative database. This methodology also allows for easier comprehension of the performance and the improvement that is needed.

KPI's specific to unit or specialty are contemplated by this disclosure and may include one or more of the following: a Pediatrics/PICU/NICU Index, an Oncology Index, a Med/Surg Index, a Women's Health Index (Labor and Delivery, Ante and Post Partum), and a Critical Care Index. As alluded to previously, system 10 is able to monitor trending KPI scores (e.g., including any of the following Intervals: 4, 6, 8 or 12 hour trend; shift trend; 24 hour trend). In some embodiments, the nurse call equipment 14 displays the following index scores (defined above) on the display of master nurse station 28, on the displays of room stations 32, and any other display board such as status board 50: Call Volume Index, Total Response Time Index, Patient Encounter Index, Direct Patient Care Index, Bed Engagement Index, Bed Safety Index, and Rounding Compliance Index.

If the nurse call server 26 or patient experience server 46 detects a trending index score below average (or a specific index value as pre-determined by the customer) in any of the proceeding measures or combination of these for a particular patient, the patient experience module initiates an alert or notification via wireless communication to staff, email, or text in any one or more of the manners described above. The patient experience module also initiates a signal to light a specific color of the associated dome light 34 to provide a visual indicator of a low trending score in some embodiments. In some embodiments, caregivers are able to acknowledge the notification of below average or poor scores using the caregiver's wireless device 52, 54, 56, 58 and/or one or more room stations 32.

Figure 3:
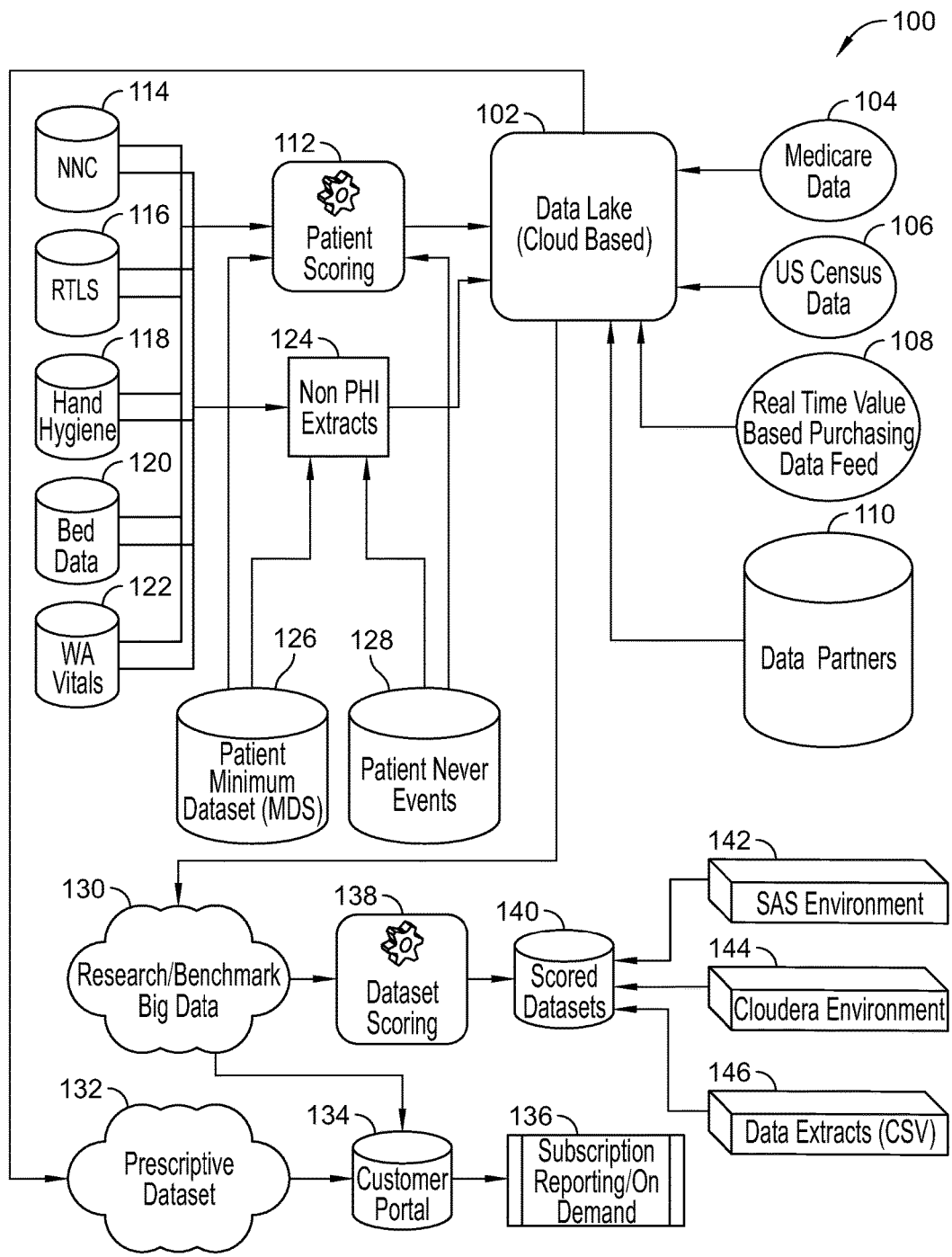
FIG. 3 is a block diagram of a data mining system that is used to research and benchmark data from a variety of sources to determine thresholds for the performance parameters that correlate to high patient satisfaction.

Referring now to FIG. 3, a data mining system 100 is shown. System 100 is used to research and benchmark data from a variety of sources to determine thresholds for the performance parameters of the type that were mentioned above and that correlate to high patient satisfaction. System 100 includes a data lake 102 which may be a cloud based data lake 102 in some embodiments. Data lake 102 comprises one or more computer devices, such as servers, that have fairly large memory capacity for storing data received from a variety of sources. For example, data lake 102 receives Medicare data 104, United States Census data 106, and other data such as data provided by the illustrative real time value based purchasing data feed 108. Data lake 102 also receives data from one or more data partners 110 in the illustrative example.

A patient scoring engine 112 also provides data to data lake 102. Engine 112 comprises one or more servers that receive and store data provided in patient experience surveys, such as the HCAHPS survey for example. In some embodiments, several healthcare facility databases provide data to patient scoring engine 112. In the illustrative example of FIG. 3, such healthcare facility databases include a nurse call database 114, a RTLS database 116, a hand hygiene database 118, a bed database 120, and a vital signs database 122. Databases 114, 116 include data accumulated by servers 26, 38 described above. Some of the data received by engine 112 from databases 114, 116, 118, 120, 122 is Protected Health Information (PHI) that needs to be handled in compliance with HIPAA standards for patient confidential information. In some embodiments, the scoring of the incoming data by engine 112 converts the PHI data into non PHI data that is, in turn, transmitted or otherwise provided to data lake 102.

Hand hygiene database 118 accumulates data relating to a hand hygiene system of the type shown and described in U.S. Pat. No. 6,727,818 which is hereby incorporated herein by reference to the extent not inconsistent with the present disclosure which shall control as to any inconsistencies. Bed data base 120 accumulates data relating to the operation of beds 16 as shown and described, for example, in U.S. Patent Application Publication No. 2012/0316892 which is hereby incorporated herein by reference to the extent not inconsistent with the present disclosure which shall control as to any inconsistencies. Vital signs database 122 accumulates data from various pieces of vital signs equipment.

Patient scoring engine 112 passes some or all of the data from one or more of databases 114, 116, 118, 120, 122 to data lake 102 in some embodiments. Engine 112 also passes patient scoring data to data lake 102. In the illustrative example, a non Protected Health Information (PHI) Extracts server 124 also receives data from databases 114, 116, 118, 120, 122. In the illustrative example, a patient minimum dataset (MDS) database 126 and a patient never events database 128 is coupled to each of patient scoring engine 112 and non PHI extracts server 124. Non PHI extracts server 124 is another source of data that is provided to data lake 102. Patient never events data of server 128 comprises data of the type listed by the National Quality Forum (NQF) and relate to serious adverse events that are preventable such as surgery on the wrong body part, performance of an incorrect medical procedure, development of bed sores, patient falls, and the like. The Minimum Data Set (MDS) of server 126 comprises data relating to a clinical assessment of residents in Medicare or Medicaid certified nursing homes.

According to the present disclosure, the data stored in data lake 102 is researched and benchmarked as indicated diagrammatically in FIG. 3 by cloud 130. The aim of the research and benchmarking is to find data that has a high correlation with positive patient experience as indicated by patients in their patient experience surveys. Thus, computer-based analysis of the data in data lake 102 is contemplated by this disclosure for uncovering the highly correlative data points. System 100 also contemplates prescriptive analytics of the data of data lake 102 as indicated diagrammatically in FIG. 3 by cloud 132. Prescriptive analytics is used for predicting future events based on information concerning past events. Response time thresholds that are determined from the researching and benchmarking are used by the patient experience module of server 46 in system 10, for example. Thus, using location technology such as RTLS system 12 to track time spent with patients by various caregivers, algorithms can be developed that correlate with patient experience scores to predict patient satisfaction as a function of caregiver attention in the future. The data from the RTLS system may also be used, if desired, to create Pareto charts of how caregivers are spending their time and/or where caregivers are spending their time during their shifts.

Research and benchmark data 130 and prescriptive data 132 is provided to a customer portal database 134 in the illustrative example of system 100. The customer portal database is accessible to subscribers as indicated at block 136 in FIG. 3. The subscribers may receive subscription reports and/or on demand data in some embodiments. System 100 also includes a data set scoring engine 138 that receives the research and benchmark data 130 to create a scored datasets database 140 as shown in FIG. 3. The scored datasets database 140 is made available to end users having, for example, a Statistical Analysis Software (SAS) Environment 142, a Cloudera Environment 144, and a Data Extracts Comma Separated Values (CSV) database 146.

According to the present disclosure, various dashboards, scorecards, reports and the like (referred to collectively as "reports") are displayed on the display screens and GUI's of various computer devices of system 10. These reports are accessible, therefore, to be viewed on GUI 29 of master nurse station 28; on the screens of devices 52, 54, 56, 58; and on screens of computers coupled to one or more of servers 26, 38, 46, 48. For example, a Shift Trending Report may be a color coded report produced at the beginning of a shift that provides the Key Performance Index scores for each patient on the floor. This report can be automated so that the leadership of a particular healthcare facility receives this report at a set time. This report, and others, can be emailed or sent to the wireless devices 52, 54, 56, 58 of specific caregivers and specific members of the leadership. In some embodiments, individual patient index scores and trending, such as a three-day trend, are displayed on the GUI's of room stations 32 for viewing by caregivers and physicians who are present in the room.

Some examples of dashboards or scorecards contemplated by the present disclosure are shown in FIGS. 5-13. FIG. 5 is an example of a first dashboard or scorecard 150 relating to patient experience performance indicators. In the illustrative example, the first column of dashboard 150 has an Index % for the following performance indicators: Patient Satisfaction, Pain Management, Patient Safety, Bed Exit, Bed Service, Q2 Turn, Vitals Doc, and Hand Hygiene. The second column of dashboard 150 includes a Trend graph (only the Trend graph for Patient Satisfaction is shown in FIG. 5). The right bar of the trend graph indicates the index value for the current shift and the three bars to the left of the current shift bar correspond to the index values of the preceding three shifts, respectively. The third column of dashboard 150 indicates the Index % for the previous shift.

FIG. 6 is an example of a second dashboard or scorecard 152 relating to number of calls per patient per shift. In the first row of scorecard 152, the first column is the count of the number of patients (30 in the illustrative example), the second column is a patient count trend graph for the current shift and three previous shifts, the third column is the number of calls per patient per shift (1.5 in the illustrative example), and the fourth column is a trend graph for the number of calls per patient per shift for the current shift and the previous three shifts. The second row of scorecard 152 includes a Leader Rounding % in the first column and a trend graph for leader rounding in the second column.

FIG. 7 is an example of a third dashboard or scorecard 154 relating to call volume and response time. These are broken up by Call Types of Pain Calls (first row of data), Potty Calls (second row of data), and Normal Calls (third row of data) in the illustrative dashboard 154. The fourth row shows information for all patient calls. Each row of data includes the number of calls, a trend graph for the number of calls for the current shift and the previous three shifts, a response time average, and a trend graph for the response time average for the current shift and the previous three shifts. In the illustrative example for the current shift, there have been 4 pain calls with an average response time of 5.5 minutes, six potty calls with an average response time of 2.5 minutes, 35 normal calls with an average response time of 3.5 minutes, and 45 total calls with an average response time of 3.4 minutes.

FIG. 8 is an example of a fourth dashboard or scorecard 156 relating to staffing and time spent by caregivers with patients. In the Staffing section of dashboard 156, there are three columns including count, ratio and trend. In the Time Spent with Patient section of dashboard 156, there are four columns including Visits, Time, Average, and Average Trend. The first four rows of dashboard 156 are broken up by caregiver types which, in the illustrative example, are Registered Nurse (RN), Patient Care Technician (PCT), Doctor (DR) and Other. The fifth row of dashboard 156 is the Total of the numbers or the overall average of the first four rows. Only the first row in the illustrative example of dashboard 156 has any trend graphs.

Figure 9:
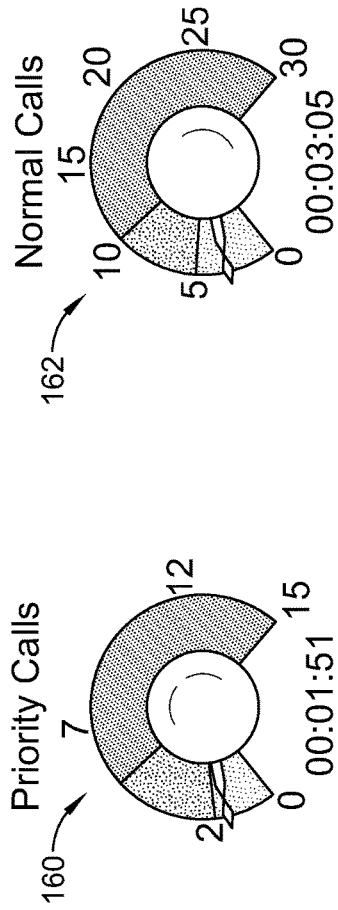
FIG. 9 is an example of a response time report screen showing response information on a room-by-room basis.

FIG. 9 is an example of a response time report screen showing a response time table 158 on a room-by-room basis. The first column of table 158 indicates the unit of the healthcare facility to which the rest of the information in table 158 relates. The second column of table 158 indicates the location or room number. The third column of table 158 indicates the average time for caregiver's to respond to calls for each room. The fourth column of table 158 indicates the maximum amount of time it took to respond to a call for each room and the fifth column of table 158 indicates the minimum amount of time it took to respond to a call for each room. The sixth column of table 158 indicates the call total for each room.

Beneath table 158 in the screen of FIG. 9 is a first pie chart 160 with a needle showing the average time to respond to priority calls for the current year and a second pie chart 162 with a needle showing the average time to respond to normal calls for the current year. In the illustrative example, the average response time for priority calls as indicated in pie chart 160 is 1 minute, 51 seconds and the average response time for normal calls as indicated in pie chart 162 is 3 minutes, 5 seconds.

Figure 10:
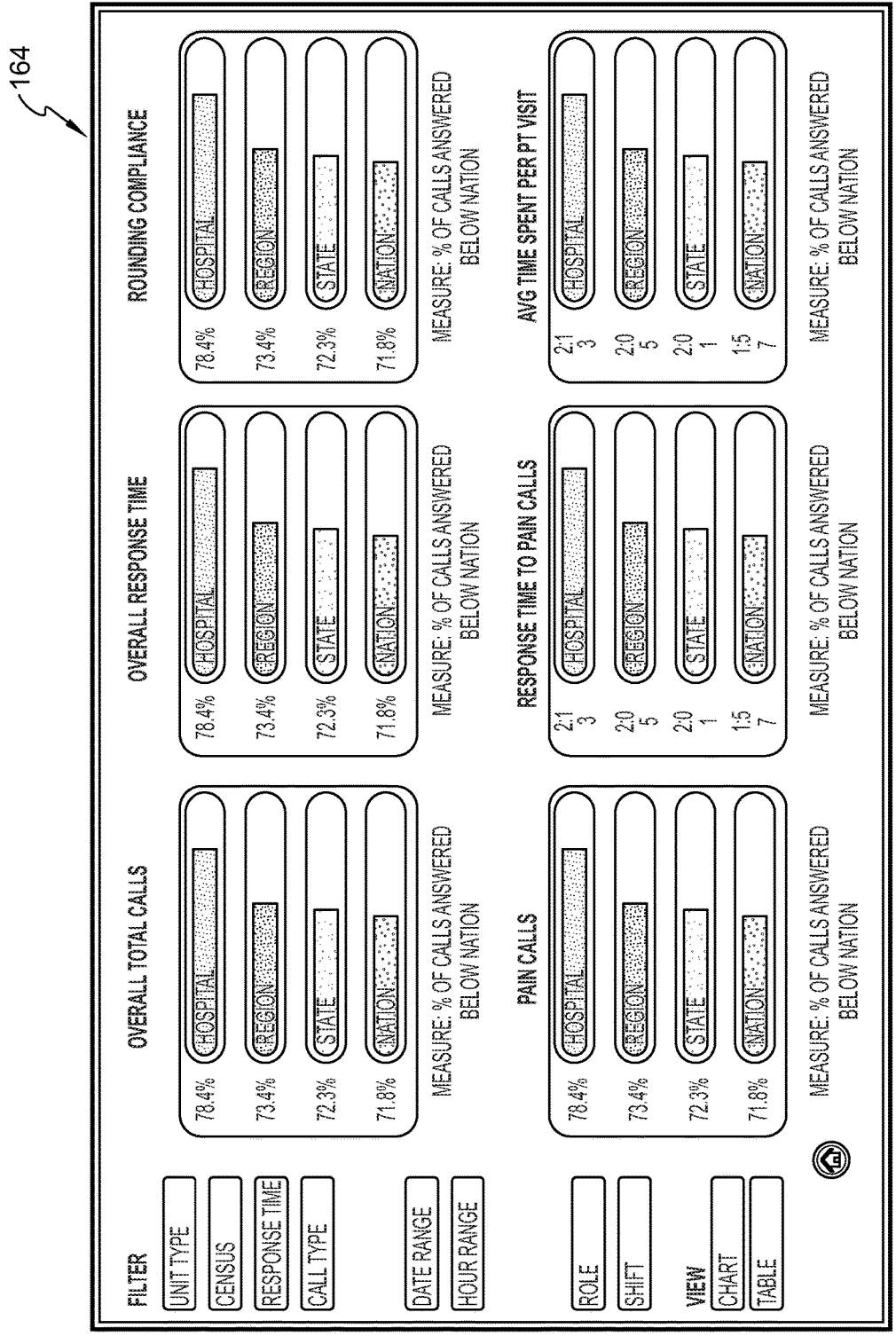
FIG. 10 is a screen shot of a real-time dashboard showing comparisons between a hospital with similar data in the region, the state and the nation for response time, rounding compliance, and average time spent per patient per visit.

FIG. 10 is a screen shot of a real-time dashboard 164 showing six horizontal bar graphs having comparisons between a hospital with similar data in the region, the state and the nation for overall total number of calls (left graph in upper row) overall response time (middle graph in upper row), rounding compliance (right graph in upper row), number of pain calls (left graph in bottom row), response time to pain calls (middle graph in bottom row), and average time spent per patient per visit (right graph in bottom row). In the illustrative example, a percentage number is given just to the left of each horizontal bar in four of the six graphs of dashboard 164 (the three graphs in the upper row and the left graph in the bottom row) and times in minutes and seconds are given just the left of each horizontal bar in two of the six graphs of dashboard 164 (the middle graph and right graph in the bottom row). To the left of the graphs of dashboard 164 are selectable fields for filtering the data in the graphs of dashboard 164 by unit type, census, response time, call type, date range, and hour range. Beneath the filter fields are view fields which are selectable so that dashboard 164 presents the data in a chart or in a table format.

FIG. 11 is a screen shot of a scorecard 166 showing week-by-week comparisons of various patient experience statistics. In the illustrative example, the first column of scorecard 166 indicates the statistic being measured. The statistics from top to bottom of the first column are for row one—Total Calls (Overall), for row two—Response Time, for row three—Pain Calls, for row four—Response Time to Pain Calls, for row five—Average Staff Encounters (Previous 24 hours) and Average Time Spent Per Patient Visit, and for row six—Rounding Compliance. The second column of scorecard 166 is Measure Type which for row one is # of Calls; for row two, three and four is # of Calls and % of Calls; for row five is # of Patient Encounters and Average Patient Visit Time; and for row six is Opportunities and Rounding Rate.

Column three of scorecard 166 indicates the numerical values for each row for the current week. Column four of scorecard indicates the numerical values for each row for the previous week. Column five of scorecard 166 indicates the % change between the current week and the previous week. Column six of scorecard 166 indicates a thirteen week average for each row. Column seven of scorecard indicates a Current Benchmark Comparison for each row. The same selectable filter fields and view fields as described above in connection with FIG. 10 also appear in FIG. 11 to the left of scorecard 166 and are used in a similar manner, as desired.

Figure 12:
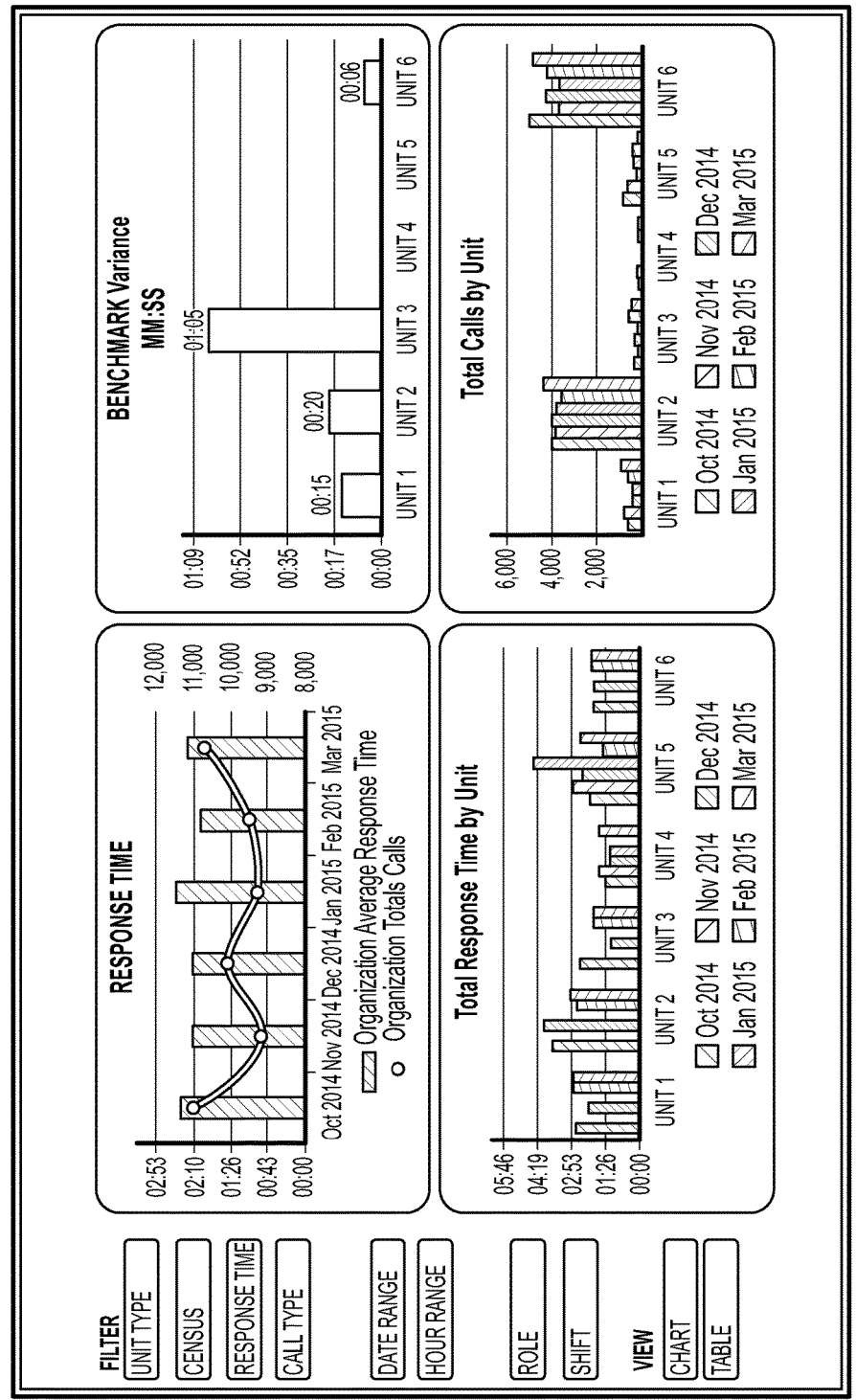
FIG. 12 is a screen shot of a historical trending screen showing four graphs relating to response times and total calls by unit.

FIG. 12 is a screen shot of a historical trending screen 168 showing four graphs relating to response times and total calls by unit. The upper left graph is shows average response time and total calls for a healthcare facility for six months. The y-axis on the left side of the upper left graph indicates response time in minutes and seconds and the y-axis on the right side of the upper left graph indicates total number of calls. Response times are shown for each month with vertical bars and number of calls are shown by circular dots superimposed on the vertical bars. The circular dots are interconnected with a curve fit line.

The upper right graph of screen 168 shows vertical bars indicating benchmark variance by unit. That is, how much time in minutes and seconds the response time exceed the benchmark for each of the units of the healthcare facility. The lower left graph of screen 168 shows, in bar graph format, Total Response Time by Unit for a six month period. Thus, each unit has six vertical bars associated therewith to indicate the average response times for all calls for each month. The vertical bars are color coded in the lower left graph for each month in the illustrative example. The lower right graph shows, in bar graph format, Total Calls by Unit for a six month period. Thus, each unit has six vertical bars associated therewith to indicate the total calls for each month. The vertical bars are color coded in the lower right graph for each month in the illustrative example. The same selectable filter fields and view fields as described above in connection with FIG. 10 also appear in FIG. 12 to the left of the four graphs and are used in a similar manner, as desired.

Figure 13:
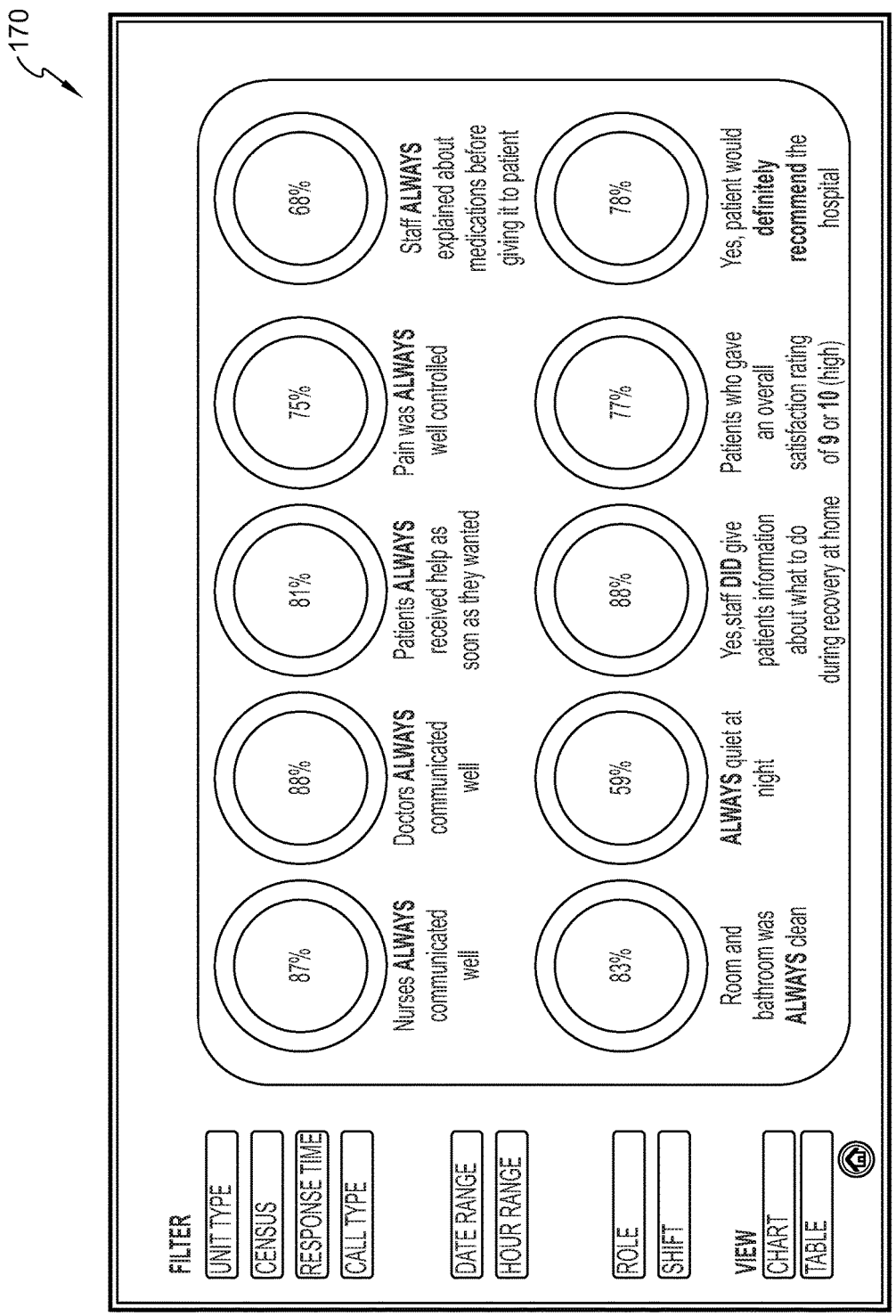
FIG. 13 is a screen shot of a patient experience portal showing percentages of affirmative answers to specific statements of patient experience surveys for a number of patients.

FIG. 13 is a screen shot of a patient experience portal screen 170 showing percentages for affirmative answers to specific statements of patient experience surveys for a number of patients. There are five specific statements in the first row of screen 170 as follows:

Nurse ALWAYS communicated well.
Doctors ALWAYS communicated well.
Patients ALWAYS received help as soon as they wanted.
Pain was ALWAYS well controlled.
Staff ALWAYS explained about medications before giving it to patient.

There are also five specific statements in the second row of screen 170 as follows:

Room and bathroom was ALWAYS clean.
ALWAYS quiet at night.
Yes, staff DID give patients information about what to do during recovery time at home.
Patients who gave an overall satisfaction rating of 9 or 10 (high).
Yes, patient would definitely recommend the hospital.

A circle above each statement indicates the percentage affirmative responses to the above-listed ten statements. The same selectable filter fields and view fields as described above in connection with FIG. 10 also appear in FIG. 13 to the left of scorecard 166 and are used in a similar manner, as desired.

Figure 14:
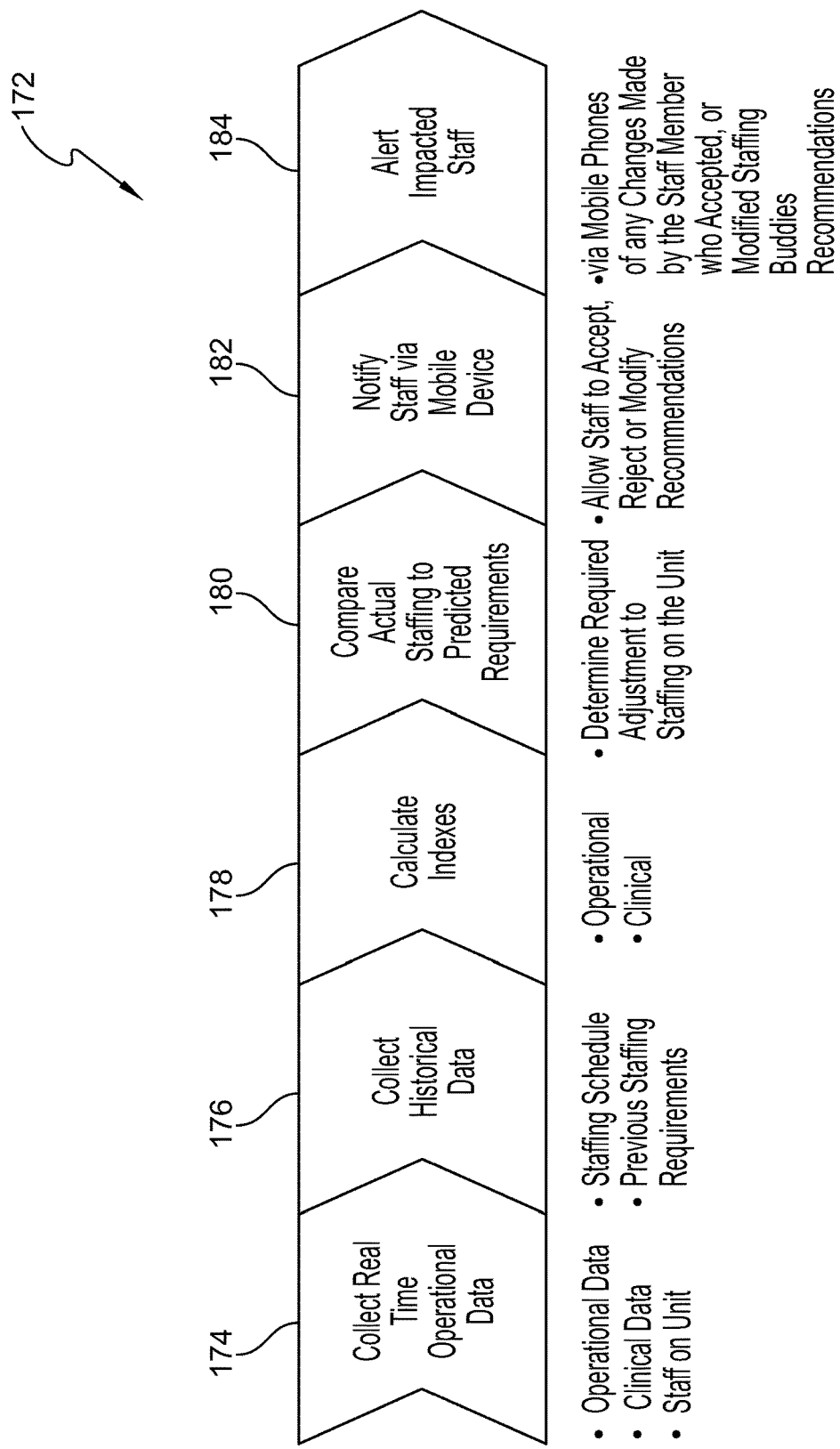
FIG. 14 is a flow diagram relating to a method of analysis of staffing levels and patient experience in a healthcare facility.

Referring now to FIG. 14, a flow diagram relating to a method 172 of analysis of staffing levels and patient experience in a healthcare facility is shown. One step of the method 172 is to collect real time operational data, including clinical data and data regarding staff on a particular unit of a healthcare facility, as indicated at block 174. Another step of the method 172 is to collect historical data, including historical data regarding staff schedule and previous staffing requirements, as indicated at block 176. With the data obtained at blocks 174, 176, the next step of the method 172 is to calculate indexes, including operational indexes and clinical indexes, as indicated at block 178. The method 172 also includes comparing actual staffing to predicted requirements, as well as determining required adjustment to staffing on the unit, as indicated at block 180. Still further, the method 172 includes notifying staff via a mobile device (e.g., one of devices 52, 54, 56, 58) as to staffing adjustments as well as allowing staff to accept, reject, or modify the staffing adjustment recommendations as indicated at block 182. Finally, the method 172 includes alerting impacted staff, such as alerting via a mobile phone 56 of any changes made by one or more staff members who have accepted or modified one or more of the staffing adjustment recommendations as indicated at block 184.

Figures 15, 16:
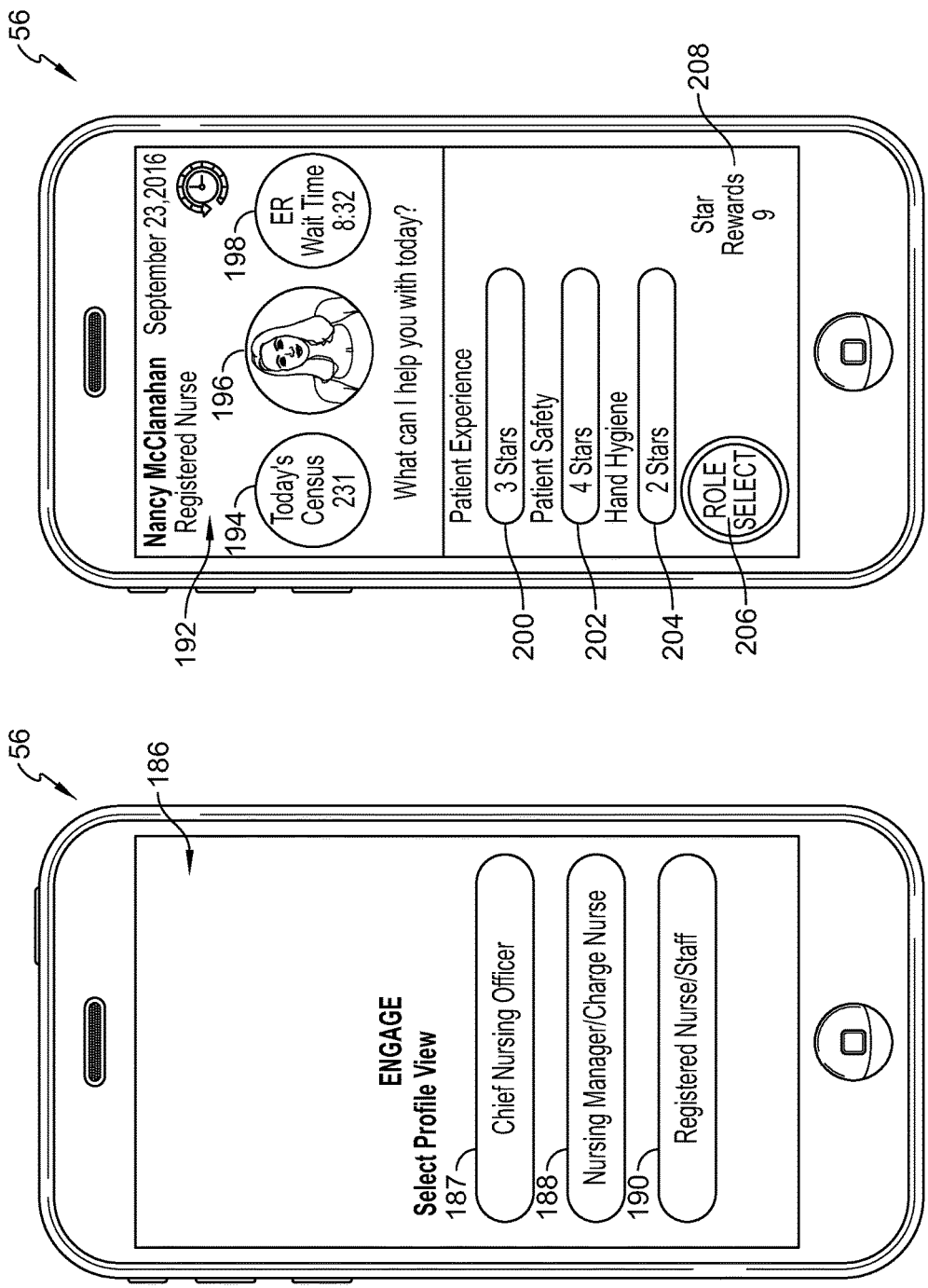
FIG. 15 is a screen shot of a home screen of a nurse and patient experience data application as displayed on a smart phone.
FIG. 16 is a screen shot of an informational overview screen for a registered nurse as displayed on a smart phone.

Referring now to FIG. 15, a screen shot of a home screen 186 of a nurse and patient experience data application is displayed on one of smart phones 56. Home screen 186 becomes displayed on phone 56 in response to a thumbnail type icon (not shown) associated with the data application being selected on the phone 56. Home screen 186 includes a Nursing Manager/Charge nurse button or icon 188 and a Registered Nurse/Staff button or icon 190 that are selectable to navigate to additional screens discussed below. Although the screens that are shown and described in connection with FIGS. 15-34 appear on smart phone 56, it should be appreciated that it is within the scope of the present disclosure for screens with the same or substantially similar information to be displayed on devices 52, 54, 58 and/or computer devices coupled to servers 26, 38, 46, 48, 60, 64, 66 and/or master nurse station 28 and/or room station 32 and/or any displays included on beds 16.

In response to selection of button 190 on screen 186, an informational overview screen 192 for a registered nurse, an arbitrary example of which is shown in FIG. 16, is displayed on smart phone 56. An upper portion of screen 192 includes a census field 194, a picture field 196, and an ER wait time field 198. Field 194 displays information about the census (e.g., total number of patients) of the associated healthcare facility. Field 196 displays a picture of the user of phone 56. Field 198 displays information about wait time (e.g., average wait time or wait time until the next emergency room (ER) is available) for the ER. Above fields 194, 196, 198, screen 192 displays the name of the staff person, the role of the staff person, and a date. In the illustrative example, the staff person's name using phone 56 is Nancy McClanahan and her role is registered nurse. The date in the example is Sep. 23, 2016. Beneath fields 194, 196, 198 is the text "What can I help you with today?" and the user is able to select that text to navigate to various help screens and help information.

Beneath the upper portion of screen 192, there are three graphical bars, namely, a patient experience bar 200, a patient safety bar 202, and a hand hygiene bar 204. Bars 200, 202, 204 each indicate a number of stars to provide a rating for the individual caregiver's performance in the enumerated area. The patient experience rating in bar 200 relates to the information described in connection with FIG. 17 below, the patient safety rating in bar 202 relates to the information described in connection with FIG. 18 below, and the hand hygiene rating in bar 204 relates to the information described in connection with FIG. 19 below. The length of each of bars 200, 202, 204 corresponds to the rating (e.g., 2, 3, or 4 stars) received in the respective area. At the bottom of screen 192, a role select icon or button 206 and a star rewards icon or button 208 is displayed. Selection of button 206 on screen 192 returns the user back to screen 186 of FIG. 15. Selection of button 208 results in a rewards center screen, discussed below in connection with FIG. 20, being displayed on smart phone 56.

Figure 17:
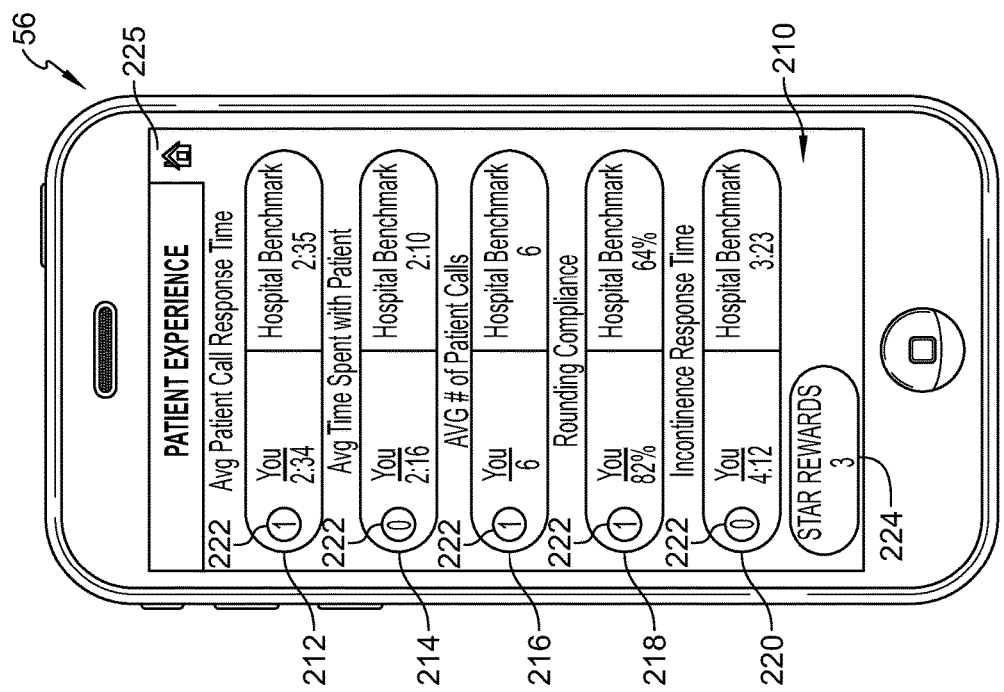
FIG. 17 is a screen shot of a first patient experience screen as displayed on a smart phone.

Selection of patient experience bar 200 on screen 192 of FIG. 16 by the user results in a patient experience screen 210, an arbitrary example of which is shown in FIG. 17, being displayed on smart phone 56. Screen 210 includes fields 212, 214, 216, 218, 220 that contain information which contributes to the user's patient experience score or rating. In particular, field 212 contains average patient call response time including the user's average response time on the left side of field 212 and a hospital benchmark on the right side of field 212. Field 214 contains average time spent with the patient including the user's average time spent on the left side of field 214 and a hospital benchmark on the right side of field 214. Field 216 contains average number of patient calls including the user's average number on the left side of field 215 and a hospital benchmark on the right side of field 216.

Still referring to FIG. 17, field 218 contains rounding compliance percentage information including the user's rounding compliance percentage on the left side of field 218 and a hospital benchmark on the right side of field 218. Field 220 contains an incontinence response time (i.e., response time to respond to an incontinence alert generated by an incontinence monitoring system) including the user's incontinence response time on the left side of field 220 and a hospital benchmark on the right side of field 220.

Near the left edge of each field 212, 214, 216, 218, 220, a rewards points bubble 222 is provided to indicate how many rewards points or stars the user has obtained based on their individual performance against the respective hospital benchmarks. In the illustrative example, the user has achieve one rewards star in connection with her performance associated with fields 212, 216, 218 and zero rewards stars in connection with her performance associated with fields 214, 220. A field 224 indicating the total number of star rewards for the user's patient experience performance is displayed beneath field 220. In the illustrative example, there are three star rewards in field 224 which matches the number of patient experience stars shown in field 200 of screen 192 of FIG. 16. A home icon or button 225 is provided at the top right of screen 210 for selection by the user to return back to screen 192 of FIG. 16 for subsequent navigation to other screens.

Figure 18:
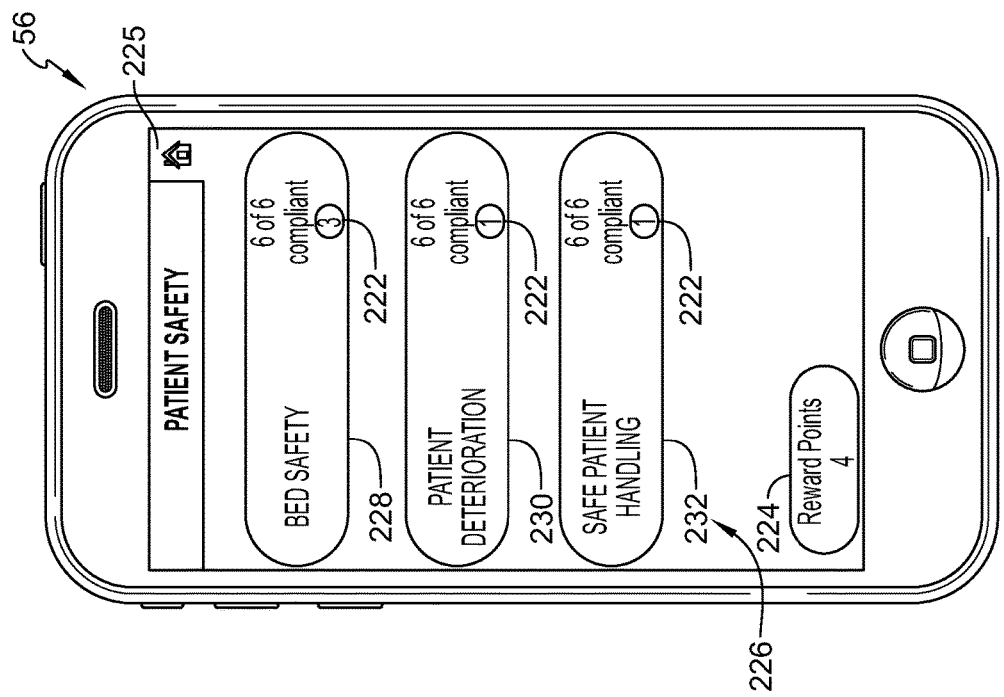
FIG. 18 is a screen shot of a first patient safety screen as displayed on a smart phone.

Selection of patient safety bar 202 on screen 192 of FIG. 16 by the user results in a patient safety screen 226, an arbitrary example of which is shown in FIG. 18, being displayed on smart phone 56. Screen 226 includes fields 228, 230, 232 that contain information which contributes to the user's patient safety score or rating. In particular, field 228 has information concerning bed safety (e.g., beds in each assigned patient's room being set up in the proper configuration such as siderails up, caster brakes set, bed in low position, bed exit/PPM system armed, etc. depending upon the acuity level of the patient); field 230 has information concerning patient deterioration; and field 232 has information concerning safe patient handling. In the illustrative example, the user was compliant in all six out of six assigned rooms for the performance criteria associated with each of fields 228, 230, 232.

Fields 228, 230, 232 also include rewards points bubble 222 which is the same as described above for indicating how many rewards points or stars the user has obtained based on their individual performance in connection with the performance criteria associated with the respective fields 228, 230, 232. Furthermore, screen 226 also has field 224 which is the same as described above for indicating the total number of star rewards for the user's patient experience performance In the illustrative example, there are four star rewards in field 224 of screen 226 which matches the number of patient safety stars shown in field 200 of screen 192 of FIG. 16. Screen 226 also has home icon 225 which is selectable as described above to return the user back to screen 192 of FIG. 16.

Figure 19:
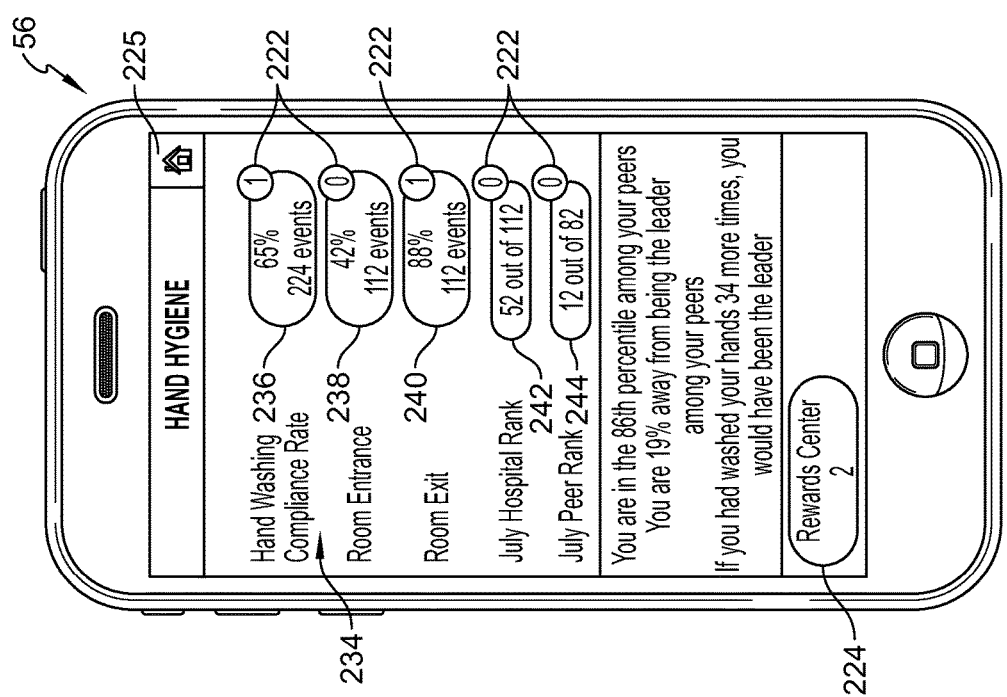
FIG. 19 is a screen shot of a first hand hygiene screen as displayed on a smart phone.

Selection of hand hygiene bar 204 on screen 192 of FIG. 16 by the user results in a hand hygiene screen 234, an arbitrary example of which is shown in FIG. 19, being displayed on smart phone 56. Screen 234 contains hand wash compliance percentage fields 236, 238, 240, a hospital rank field 242, and a peer rank field 244 that contain information which contributes to the user's hand hygiene compliance performance In particular, field 236 contains the user's overall handwashing compliance rate, as a percentage, according to the handwashing protocol of the associated healthcare facility. For example, some healthcare facilities have wash-in protocols requiring caregivers to wash their hands within a threshold amount of time of entering a patient room; some healthcare facilities have wash-out protocols requiring caregivers to wash their hands within a threshold amount of time, which may be the same as, or different than, the wash-in time threshold, of exiting a patient room; and some healthcare facilities have both wash-in and wash-out protocols. In this regard, field 238 contains the user's compliance rate, as a percentage, with regard to a wash-in or room entrance protocol and field 240 contains the user's compliance rate, as a percentage, with regard to a wash-out or room exit protocol.

Still referring to FIG. 19, field 242 contains information regarding how the user's healthcare facility or hospital ranked as compared to a larger set of healthcare facilities or hospitals with regard to hand washing compliance. The larger set may be other facilities that are owned by the same parent corporation or other facilities within a geographic region (e.g., a state or part of a state) or other facilities that have decided to share hand washing compliance information with each other for comparison purposes. Field 244 contains information regarding how the user's hand washing compliance rate compared to others of the user's peers. The peers may be other employees of the same healthcare facility as the user, such as employees having the same role (e.g., registered nurse, nurse manager, therapist, physician, etc.), or may be other employees of a larger set of healthcare facilities or hospitals. Similar to screens 210, 226, screen 234 of FIG. 19 also has rewards points bubbles 222, a total rewards field 224, and a home button 225 which contain information or operate in the same manner as described above, except that field 224 on screen 234 shows the reward points or stars total for the bubbles 222 appearing on screen 234.

Figure 20:
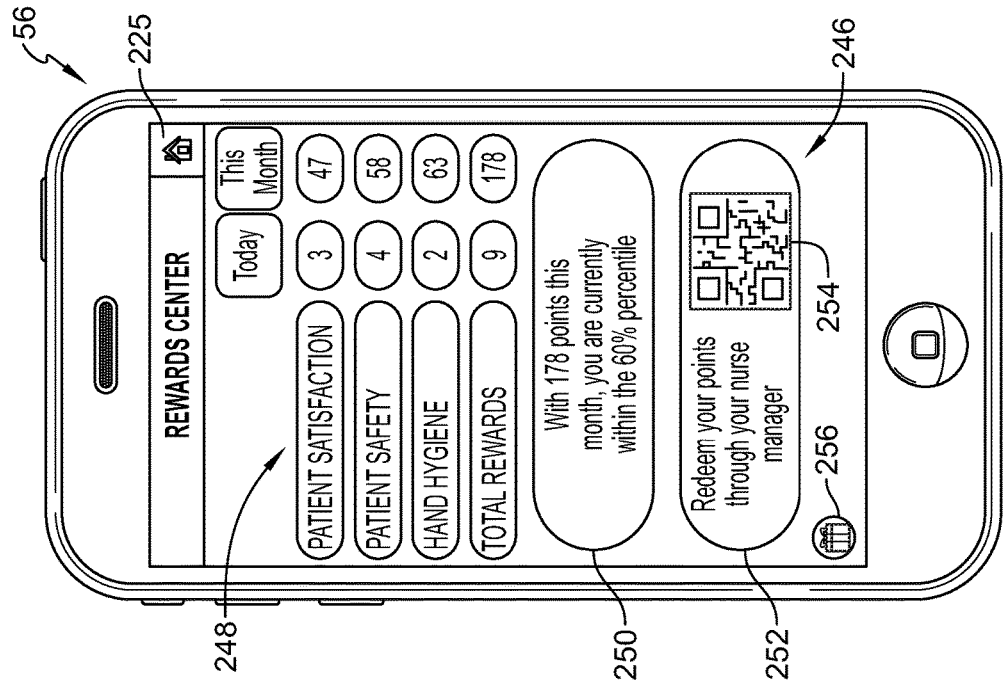
FIG. 20 is a screen shot of a first rewards center screen as displayed on a smart phone.

Selection of star rewards field 208 on screen 192 of FIG. 16, or selection of rewards points field 224 on any of screens 210, 226, 234 of respective FIGS. 17-19, by the user results in a rewards center screen, an arbitrary example of which is shown in FIG. 20, being displayed on the user's smart phone 56. Screen 246 has a table 248 that includes three columns. The left hand column has row titles which are, from the top of table 248 to the bottom of table 248, labeled as patient satisfaction, patient safety, hand hygiene, and total rewards. The middle column has the number of rewards points earned by the user for each of the corresponding rows for the current day. The right hand column has the number of rewards points earned by the user for each of the corresponding rows for the current month.

Still referring to FIG. 20, a rewards center summary field 250 is displayed beneath table 248 and contains a message indicating the user's total number of rewards points for the month and a percentile ranking of the user's total rewards points as compared to other users. In the illustrative example, the message in field 250 states, "With 178 points this month, you are currently within the 60% percentile." Beneath field 250 is a points redemption field 252 that contains a 2-dimensional (2D) bar code 254 and a message which states, "Redeem you points through your nurse manager." The 2D bar code is read by a reader and a menu of items, coupons, gift cards, food, beverages, cash amount, or other rewards appears on a screen for selection by the user. Screen 246 also has a gift icon or button 256 which is selectable by the user to give the user's reward points to another user or to a charitable organization, for example. Screen 246 also has home icon 225 which operates in the same manner as described above.

In response to selection of button 188 on screen 186 of FIG. 15, an informational overview screen 258 for a nurse manager, an arbitrary example of which is shown in FIG. 21, is displayed on smart phone 56. An upper portion of screen 258 includes census field 194, picture field 196, and ER wait time field 198. Which are basically the same as the like fields on screen 192 of FIG. 16 and so the same reference numbers are used in FIG. 21. The description above of fields 194, 196, 198 in connection with FIG. 16 is equally applicable to FIG. 21. Above fields 194, 196, 198, screen 258 displays the name of the staff person, the role of the staff person, and a date. In the illustrative example, the staff person's name using phone 56 is Christina Smith and her role is nurse manager. The date in the example is Sep. 23, 2016. Beneath fields 194, 196, 198 are a first informational bar 260 which indicates the number of caregivers for which the nurse manager is supervising and the total number of patients assigned to those caregivers. In the illustrative example of bar 260, the nurse manager is supervising 6 caregivers who have been assigned a total of 35 patients. A second informational bar 262 appears just beneath bar 260 and indicates the caregiver to patient ratio. In the illustrative example of bar 262, the information "1:6 Patient Ratio Today" appears.

Beneath the bar 262 of screen 258 of FIG. 21, there are three graphical bars, namely, a patient experience bar 264, a patient safety bar 266, and a hand hygiene bar 268. Bars 264, 266, 268 each indicate an average number of stars to provide an average rating for all of the caregivers being supervised by the nurse manager regarding their performance in the enumerated area. The patient experience ratings contributing to bar 264, the patient safety ratings contributing to bar 266, and the hand hygiene ratings contributing to bar 268 relate to the information described above in connection with FIGS. 17-19 for each of the caregivers being supervised. The length of each of bars 264, 266, 268 corresponds to the rating average of the supervised caregivers (e.g., 2, 4, or 4.5 stars) received in the respective area.

Beneath bar 268 on screen 258 of FIG. 21, high star patients field 270 is displayed and indicates the number of high star patients who have given the highest rating possible in connection with a patient experience survey. In the illustrative example of field 270, out of the 35 total patients, five have given a high star rating. At the bottom of screen 258, the role select icon or button 206 is provided for selection to return back to screen 186 of FIG. 15 in the same manner as described above in connection with screen 192. A star rewards icon or button 274 is also displayed at the bottom of screen 258. Selection of button 274 results in a rewards center screen, discussed below in connection with FIG. 26, being displayed on smart phone 56.

Selection of patient experience bar 264 on screen 258 of FIG. 21 by the user results in a patient experience screen 276, an arbitrary example of which is shown in FIG. 22, being displayed on smart phone 56. Similarly, selection of patient safety bar 266 on screen 258 of FIG. 21 by the user results in a patient safety screen 278, an arbitrary example of which is shown in FIG. 23, being displayed on smart phone 56. Further similarly, selection of hand hygiene bar 268 on screen 258 of FIG. 21 by the user results in a hand hygiene screen 280, an arbitrary example of which is shown in FIG. 24, being displayed on smart phone 56. Each of screens 276, 278, 280 of FIGS. 22-24 displays information in a similar format. In particular, in the illustrative example, screens 276, 278, 280 each have caregiver fields for the six caregivers being supervised by the nurse manager. In each of the caregiver fields, the particular caregiver's name appears along with a today bar 282 indicating today's number of stars for the associated performance criteria and a yesterday bar 284 indicating yesterday's number of stars for the associated performance criteria. Each of screens 276, 278, 280 also has a menu bar 286 above the list of caregiver fields for selection by the nurse manager of menu items including Top 5 Performers, All Staff, and Bottom 5 Performers. Selection of one of the menu items causes the associated list of caregivers (i.e., top five, all or bottom five) being displayed on phone 56. Screens 276, 278, 280 also each have a home icon or button 288, the selection of which returns the user to screen 258 of FIG. 21.

Selection of star rewards button 274 on screen 258 of FIG. 21, results in a rewards center screen 300, an arbitrary example of which is shown in FIG. 25, being displayed on a smart phone 56. Screen 300 has a last month's daily average stars field 302, a last month's total stars field 304, a this month's average stars field 306, and a this month's total stars field 308. Fields 302, 306 indicate, for the previous month and the current month, respectively, the average number of stars obtained per day by all of the caregivers being supervised by the nurse manager. Fields 304, 308 indicate, for the previous month and the current month, respectively, the total number of stars obtained for the month by all of the caregivers being supervised by the nurse manager. Screen 300 also has a Top 3 Performers table 310 which lists the names of the three caregivers with the most rewards points or stars for the current month along with the number of stars or points for each top performing caregiver. Screen 300 further has a Bottom 3 Performers table 312 which lists the names of the three caregivers with the least amount of rewards points or stars for the current month along with the number of stars or points for each bottom performing caregiver. Screen 300 has home icon 288, the selection of which returns the user to screen 258.

In some embodiments contemplated by this disclosure, competitions between teams of caregivers (e.g., first shift, second shift, third shift and/or unit 1, unit 2, unit 3) are conducted to determine which team is providing the best patient experience. In some such competitions, the rewards points are analyzed by server 46, for example, for the various team members. Such analysis may include tallying the total number of rewards points for the team members and comparing the totals of the various teams in the competition and/or determining the average number of reward points per team member. In this latter scenario, the team with the highest average rewards points is considered the winner. Competitions that are based on particular measured parameters (e.g., average response time to answer nurse calls or number of calls answered per shift) rather than rewards points totals or averages are also within the scope of this disclosure. The winning team may receive additional rewards points and/or a cash award and/or extra time off. Such competitions may provide team motivation to build a better work environment and enhance the overall patient experience.

FIG. 26 is a screen shot of a patient satisfaction screen which may be displayed on smart phone 56 in lieu of the patient experience screen 210 of FIG. 17. Basically, the only difference between the screen of FIG. 27 and screen 210 of FIG. 17 is the heading at the top of the screen. Accordingly, the same reference numbers are used in FIG. 26 as are used in FIG. 17.

Figure 27:
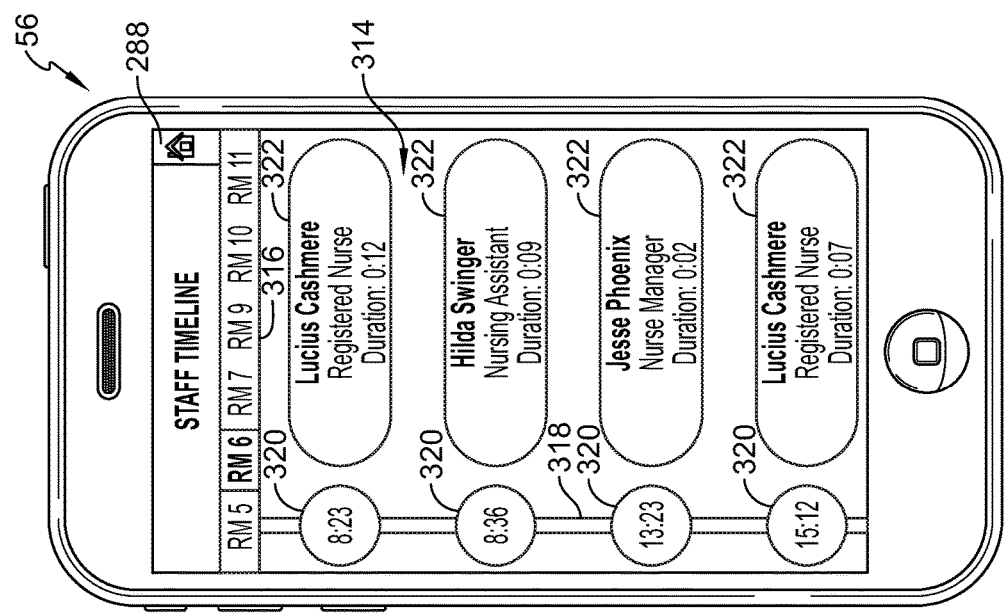
FIG. 27 is a screen shot of a staff timeline screen as displayed on a smart phone.

FIGS. 27-33 depict arbitrary examples of additional informational screens to which a nurse manager has access. The nurse manager may navigate to the screens of FIGS. 27-33 by any suitable selection on screens 258, 276, 278, 280, 300 of FIGS. 21-25 at the discretion of the programmer. For example, a staff timeline screen 314 is shown in FIG. 27 and may be displayed on smart phone 56 in response to selection of today's census filed 194 on screen 258 of FIG. 21 or via swiping with a user's finger left or right on any of screens 276, 278, 280 of FIGS. 22-24 just to name a couple of examples.

Screen 314 of FIG. 27 includes a room menu bar 316 at the top of the screen 314 for selection of a room number for which a timeline is to be shown. Menu bar 316 can be scrolled left or right, by swiping for example, so that other rooms can be seen on menu bar 316. In the illustrative example, room (RM) 6 has been selected resulting in a vertically oriented time line 318 appearing on screen 314 with a series of time bubbles 320 shown along the timeline 318 with the times, in hours:minutes format, at which caregivers visited the selected room, being indicated in each bubble. 320. Timeline 318 can be scrolled up and down, such as by swiping, to see other bubbles 320 of caregiver visits to the selected room occurring at other times. Adjacent to each time bubble 320 is a field 322 having the name of caregiver who visited the room at the time indicated in the associated bubble 320, the role of the caregiver, and the duration of the visit in hours:minutes format.

Figure 28:
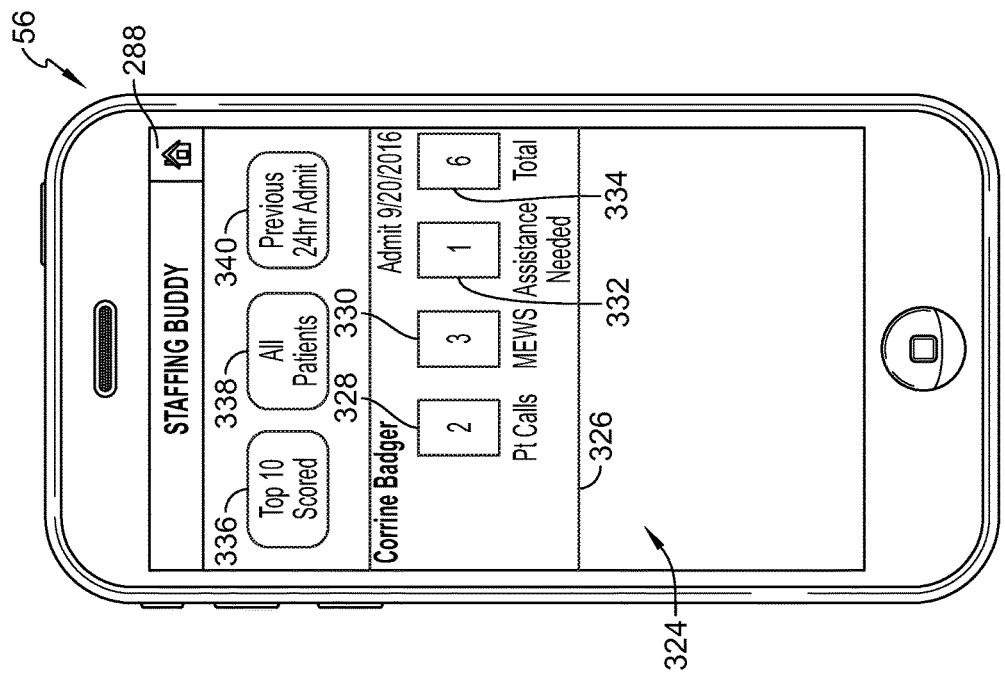
FIG. 28 is a screen shot of a first patient informational screen as displayed on a smart phone.

Referring now to FIG. 28 a first patient informational screen 324 is displayed on smart phone 56. Screen 324 is also referred to as a first "staffing buddy" screen 324. Screen 324 has a window 326 that contains information which pertains to a particular patient. In the illustrative example, window 326 pertains to the patient named Corrine Badger. Window 326 has a patient calls field 328, a modified early warning system (MEWS) score field 330, an assistance needed field 332, and a total field 334. Field 328 indicates the number of patient calls that were placed by the particular patient in the prior shift (i.e., the shift prior to the current shift). Field 330 indicates the MEWS score for the patient as measured in the prior shift. Field 332 indicates the number of times the patient needed assistance in the prior shift, such as assistance getting out of bed to go to the bathroom for example. The total field contains the sum of the numbers appearing in fields 328, 330, 332.

The higher the number in the total field 334, the more time is required by caregivers in attending to the patient's needs. Because the information in window 326 relates to events that occurred during the prior shift, it provides a predictor of how much attention the same patient may need during the current shift. When the totals from field 334 of all of the patients for which a nurse manager is assigned are analyzed, staffing decisions can be made regarding how to allocate staff members to patients during the current shift. Thus, caregivers are assigned for the current shift based on patient needs scores (i.e., the scores appearing in fields 334 of screen 324) from the previous shift. A software algorithm automatically assigns the caregivers to patients according to this disclosure. Thus, for example, caregivers may be assigned patients so that the assigned patients to each caregiver have needs scores totals that are approximately equivalent.

Other criteria that may be considered in connection with determining a patient needs score according to this disclosure, in lieu of, or in addition to, the information shown in fields 328, 330, 332, include the time spent in the patient's room by caregivers during the previous shift, number of incontinence events occurring during the previous shift, and number of bed exit and/or patient position alarms (e.g., as sensed by a bed exit or patient position monitoring (PPM) system of a hospital bed) occurring during the previous shift. Further alternatively, an early warning system (EWS) score may be used in addition to, or in lieu of, the MEWS score in connection with determining the patient needs score of field 334.

Still referring to FIG. 28, above window 326, a Top 10 Scored button or icon 336, an All Patients button or icon 338, and a Previous 24 hour (hr) Admit button or icon 340 is shown on screen 324. Selection of buttons 336, 338, 340 results in a list of patients corresponding to the name of the button 336, 338, 340 appearing on smart phone 56. Thus, the names of the top 10 scored patients appear if button 336 is selected, the names of all patients appear (or a subset thereof with scrolling capabilities to view the rest) if button 338 is selected, and the names of only those patients admitted in the previous 24 hour period appear. The patients appearing on phone 56 in response to selection of buttons 336, 338, 340 are those to which the nurse manager has been assigned and that meet the criteria associated with each of buttons 336, 338, 340.

Figures 29, 30:
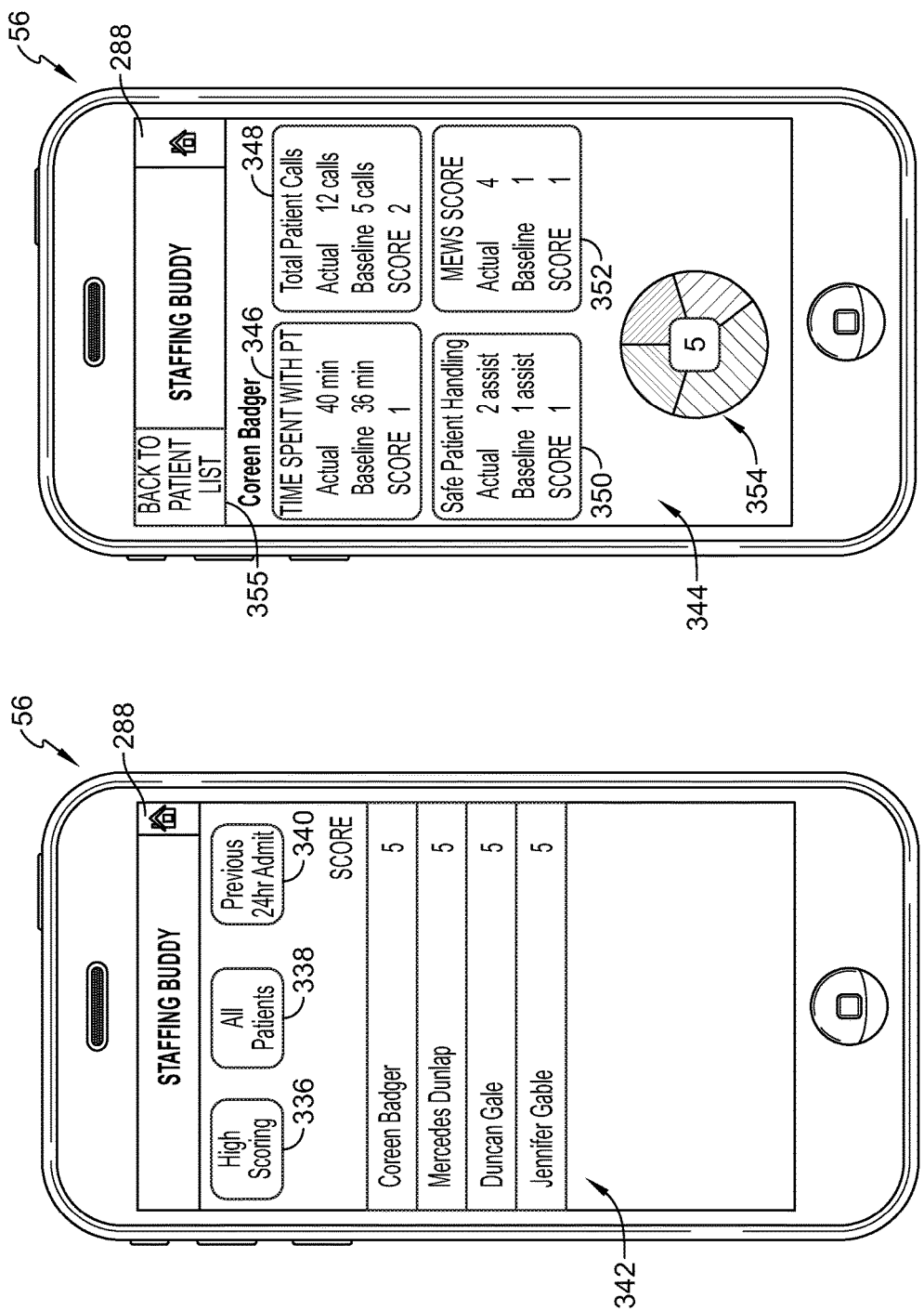
FIG. 29 is a screen shot of a second patient informational screen as displayed on a smart phone.
FIG. 30 is a screen shot of a third patient informational screen as displayed on a smart phone.

Referring now to FIG. 29, a second patient informational screen 342 is displayed on smart phone 56 in response to selection of button 336. In the illustrative example, there are only four patients that are considered to be the high scoring patients and so only the names of those four patients is shown on screen 342. The higher a patient's score, the more time that caregivers can expect to have to devote to that particular patient during their shift.

Referring now to FIG. 30, a third patient informational screen 344 is displayed on smart phone 56. Screen 344 becomes displayed on phone 56 in response to the patient's name being selected on screen 342. So, in the illustrative example, Coreen Badger's name was selected on screen 342. Screen 344 has a time spent with patient window 346, a total patient calls window 348, a safe patient handling window 350, and a MEWS score window 352. Window 346 includes the actual amount of time a caregiver has spent with the patient during a shift, a baseline amount of time that caregivers should spend with a patient, and a score for the time spent with the patient. In the illustrative example, a caregiver has spent 40 minutes with the patient, the baseline time is 36 minutes, and the score in window 346 is 1.

Window 348 includes the actual number of patient calls during a shift, a baseline number of calls that caregivers should have from a patient, and a score for the total number of patient calls. In the illustrative example, there have been 12 actual calls, the baseline number of calls is 5, and the score in window 348 is 2. Window 350 includes the actual number of patient handling assists during a shift, a baseline number of handling assists that a patient should have during a shift, and a score relating to patient handling assists. In the illustrative example, there have been 2 actual patient handling assists, the baseline number of patient handling assists is 1, and score in window 350 is 1. Window 352 includes the patient's actual MEWS score, a baseline MEWS score, and a score relating to the MEWS score. In the illustrative example, the actual MEWS score for the patient is 4, the baseline MEWS score is 1, and the patient's score in window 352 is 1.

Screen 344 of FIG. 30 has a pie chart 354 beneath windows 350, 352 that contains the patient's overall needs score in the center of the chart 354. The overall score is the sum of the scores in windows 346, 348, 350, 352. In the illustrative example, the patient's needs score is 5. Windows 346, 348, 350, 352 are color coded and the portions of chart 354 corresponding to each score from windows 346, 348, 350, 352 is color coded with the same color as the respective window 346, 348, 350, 352. Screen 344 has a back to patient list button or icon 355 which is selected by the user to return back to screen 342 of FIG. 29.

Figure 31:
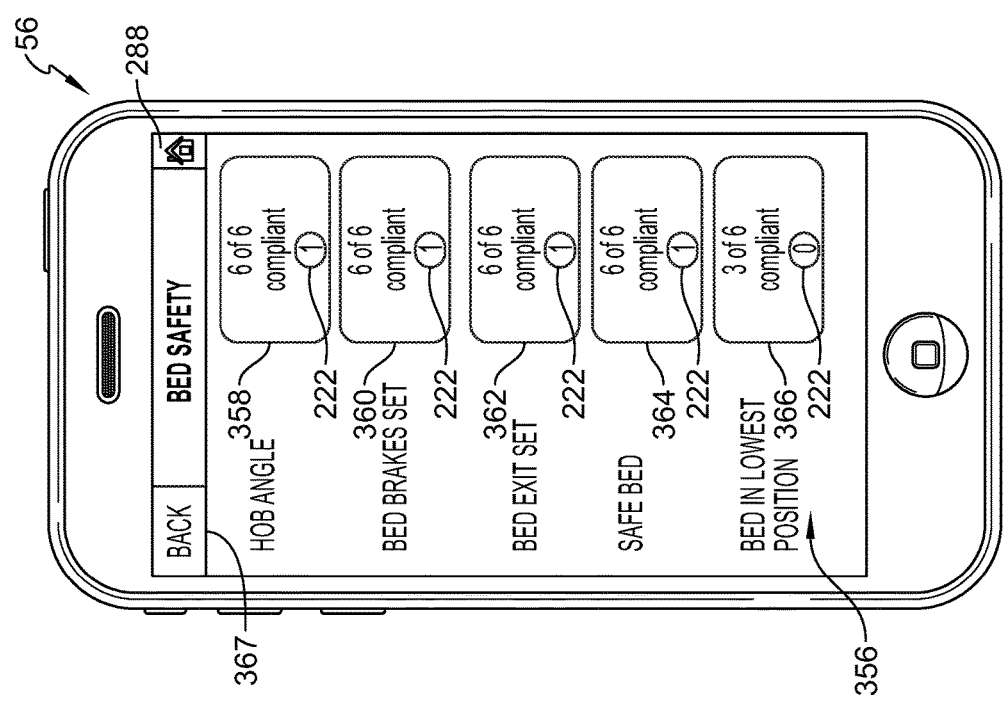
FIG. 31 is a screen shot of a bed safety screen as displayed on a smart phone.

Referring now to FIG. 31, a bed safety screen 356 is displayed on smart phone 56. Screen 356 has a head of bed (HOB) angle window 358, a bed brakes set window 360, a bed exit set window 362, a safe bed window 364, and a bed in lowest position window 366. The information in windows 358, 360, 362, 364, 366 corresponds to the status of the patient beds for each of the patients assigned to the nurse manager. In the illustrative example, there are six patient assigned. Windows 358, 360, 362, 364 each indicate that 6 of 6 beds are compliant with regard to the respective bed feature being monitored (e.g., HOB angle, bed brakes being set, bed exit system being set or armed, bed being in a safe configuration). However only 3 of 6 beds are compliant with the bed in lowest position criteria. Each of windows 358, 360, 362, 364, 366 has a rewards points bubble 222. In the illustrative example, the bubbles 222 of each of compliant windows 358, 360, 362, 364 have 1 reward point indicated and the bubble of noncompliant window 366 has zero rewards points indicated. Screen 356 has a back button or icon 367 which is selected by the user to return back to the previous screen.

Figure 32:
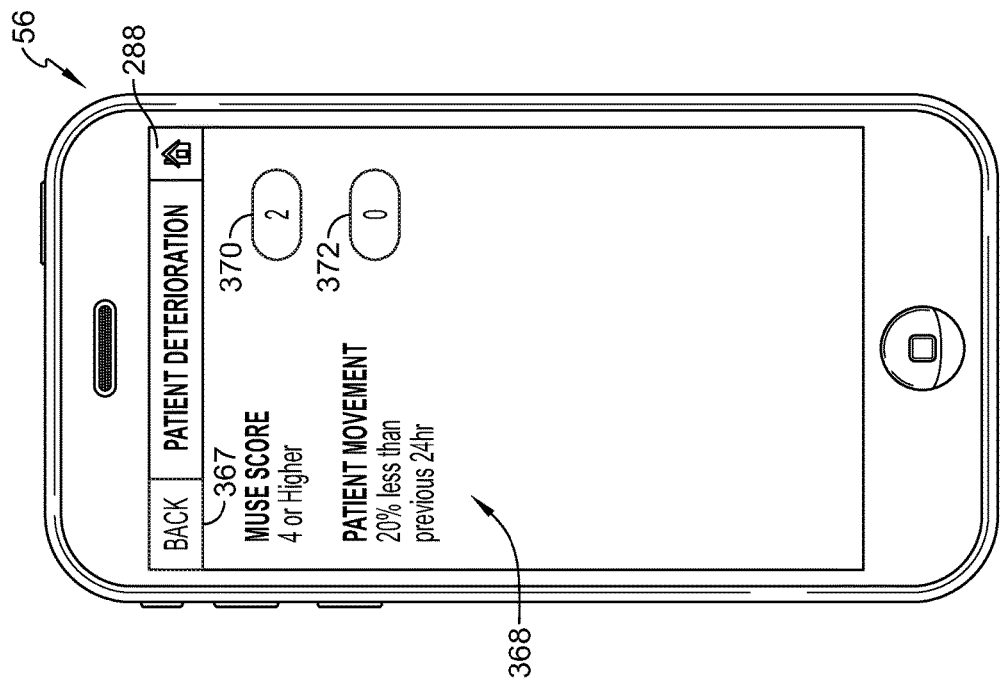
FIG. 32 is a screen shot of a patient deterioration screen as displayed on a smart phone.

Referring now to FIG. 32, a patient deterioration screen 368 is displayed on smart phone 56. Screen 368 has a MUSE Score 4 or higher field 370 which indicates the number of patients assigned to the nurse manager that have a MEWS score of 4 or higher. In the illustrative example, there are two such patients. Screen 368 also has a patient movement field 372 which indicates the number of patient handling assists or movements that have occurred during a shift. In the illustrative example, zero patients have been assisted in this regard.

Figure 33:
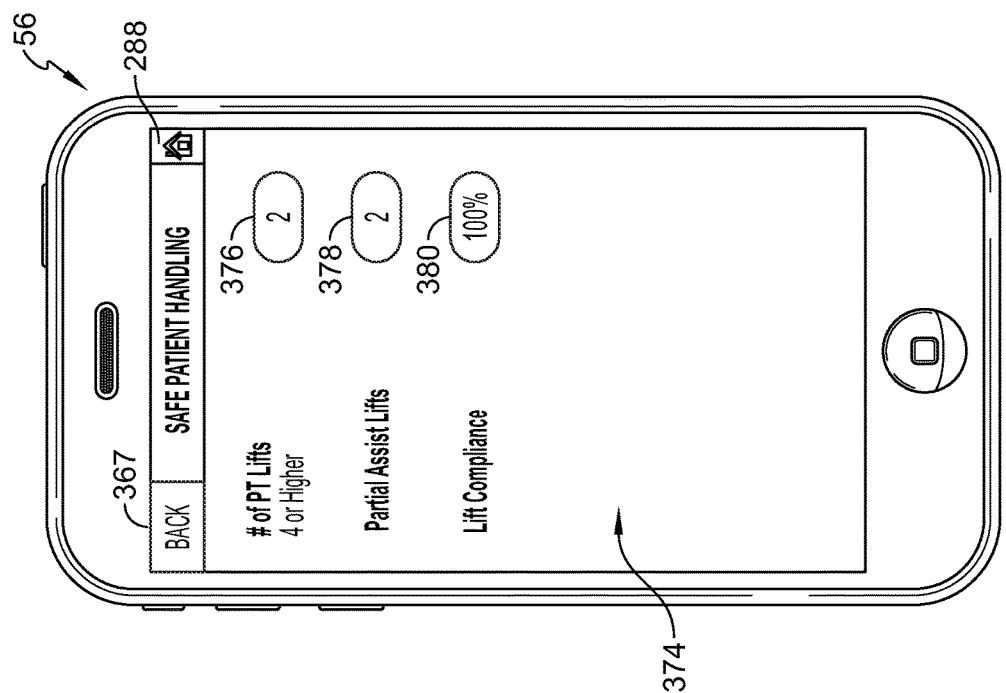
FIG. 33 is a screen shot of a safe patient handling screen as displayed on a smart phone.

Referring now to FIG. 33, a safe patient handling screen 374 is displayed on smart phone 56. Screen 374 has a number of patient lifts field 376 which indicates the number of patient lifts that have occurred during a shift. In the illustrative example, there have been two patient lifts.

Screen 374 also has a partial assists lifts field 378 which indicates the number of partial assist lifts that have occurred during a shift. In the illustrative example, two partial assist lifts have occurred. Screen 374 further has a lift compliance field 380 which indicates how many of the lifts indicated in fields 376, 378 were carried out according to the proper lift protocol.

Figure 34:
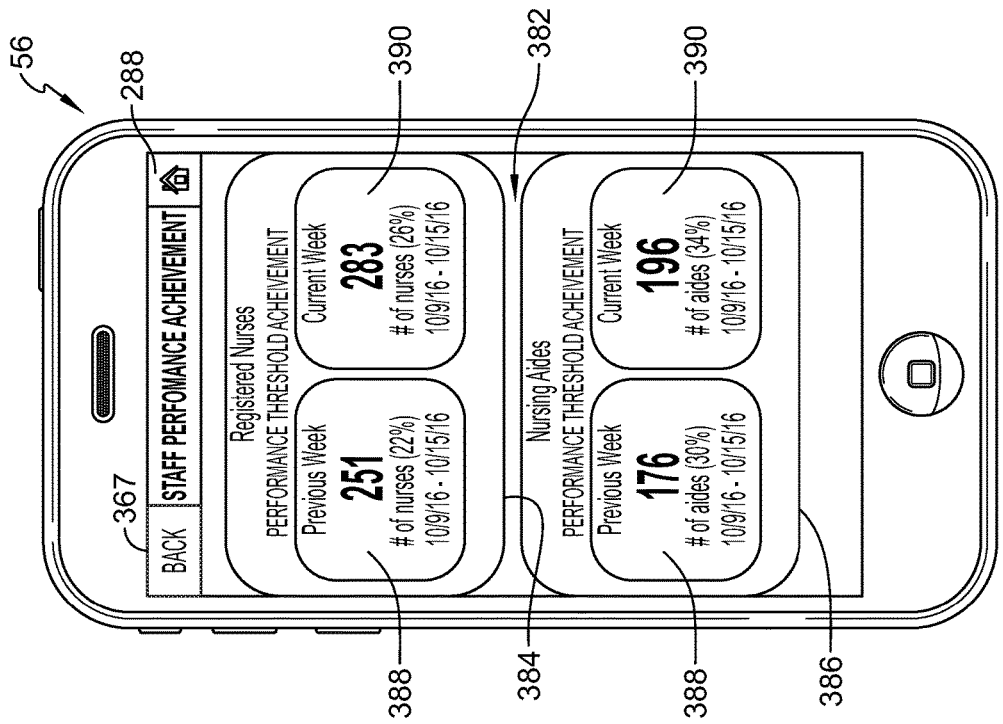
FIG. 34 is a screen shot of a staff performance achievement screen as displayed on a smart phone.

Referring now to FIG. 34, a staff performance achievement screen 382 is displayed on smart phone 56 in response to chief nursing officer button 187 being selected on screen 186 of FIG. 15. Screen 382 includes a Registered Nurses window 384 and a Nursing Aides window 386. Each of windows 384, 386 has statistics related to performance threshold achievement for the respective roles of caregivers (e.g., Registered Nurses and Nursing Aides). In particular, each of windows 384, 386 has a previous week field 388 and a current week field 390. Field 388 of window 384 indicates that in the previous week, 251 registered nurses (or 22% of registered nurses) met their performance threshold achievement targets. Field 388 of window 386 indicates that in the previous week, 176 nursing aides (or 30% of nursing aides) met their performance threshold achievement targets. Field 390 of window 384 indicates that in the current week, 283 registered nurses (or 26% of registered nurses) are meeting their performance threshold achievement targets. Field 390 of window 386 indicates that in the previous week, 196 nursing aides (or 34% of nursing aides) are meeting their performance threshold achievement targets.

It should be appreciated that data obtained from system 10 and/or system 100 is used in connection with populating the screens of FIGS. 16-34 with information and data. Thus, smart phone 56 is in communication with one or more of the various data repositories of systems 10, 100. The software functionality disclosed herein in connection with various embodiments of the patient experience module, as described above in connection with FIGS. 1-34, improves the operation of respective computer devices of systems 10, 100 themselves by providing the computer devices with functionality that is otherwise absent from the computer devices. The speed with which actionable information concerning patient experience and satisfaction is presented to caregivers is increased by the software functionality disclosed herein in connection with FIGS. 1-34. Thus, the patient experience module embodiments disclosed herein solves one or more problems that are rooted in computer technology employed in heath information systems. The software of the various embodiments of the patient experience module of the present disclosure permits managers to more quickly see relevant information so as to be able to better allocate staffing resources to patients and to put into place remedial measures based on real time performance information as compared to benchmarks which, themselves, are determined using computer technology.

According to the present disclosure, it is contemplated that patient satisfaction may be enhanced by permitting a patient to choose their own room. In some embodiments, hospital staff at a computer, such as an admission/discharge/transfer (ADT) computer, may present information to the patient regarding available rooms and received feedback from the patient regarding which room is desired. For example, the information about the patient rooms may include the amenities in the room, the type of room (e.g., private room for a single patient or semi-private for two patients), television type and size, whether the room has a chair or sofa configured for guests to sleep overnight, the view outside a window of the room, location of the room relative to the entrance or exit of the wing, proximity of the room to the master nurse station, proximity of the room to vending machines, and so forth.

In some embodiments, a patient location device such as a tag, badge, or wristband with a transmitter is given to the patient and the patient is taken to see the available rooms or is given a list of available rooms. When the patient decides on the desired room, the patient enters that room and remains in the desired room. After a threshold amount of time in the room, such as two minutes or five minutes, for example, being sensed by the RTLS system 12, the patient is automatically assigned to the desired room. In response to the room assignment, one or more caregivers are notified of the new assignment, such as receiving a message from server 60 on devices 52, 54, 56, 58, and, in some embodiments, the patient is notified that a caregiver is one the way to meet with the patient. Such a notification to the patient may be provided textually on room station 32 or on the screen of a television in the room and/or may be provided by an audio message on room station 32, bed 16, or the television in the room.

Although certain illustrative embodiments have been described in detail above, many embodiments, variations and modifications are possible that are still within the scope and spirit of this disclosure as described herein and as defined in the following claims.

The invention claimed is:

1. A system comprising
   locating equipment to track the whereabouts of caregivers in a healthcare facility,
   nurse call equipment to receive nurse call requests from patients located in patient rooms of the healthcare facility, the nurse call equipment including at least one nurse call computer that keeps track of an amount of time it takes caregivers to respond to each nurse call and that keeps track of how long at least one caregiver is present in each patient room based on information received by the nurse call computer from the locating equipment, and
   a patient experience module that receives information from the nurse call equipment regarding types of nurse calls placed by the patients, the types of nurse calls including a first call type and a second call type, the patient experience module comparing response times for each first call type to a first response time threshold and comparing response times for each second call type to a second response time threshold, the first response time threshold being a different amount of time than the second time threshold, the patient experience module initiating an alert to provide a notification that the first response time threshold or the second response time threshold has been exceeded for one or more of the first call types or the second call types, respectively, wherein at least one of the first response time threshold or the second response time threshold is established based on historical data from patient satisfaction surveys.

2. The system of claim 1, wherein the first call type is a pain call and the second call type is a normal call, the first response time threshold for the pain call being less than the second response time threshold for the normal call.

3. The system of claim 1, wherein the first call type is a potty call and the second call type is a normal call, the first response time threshold for the potty call being less than the second response time threshold for the normal call.

4. The system of claim 1, wherein the information regarding the types of nurse calls placed by the patients is entered manually by a caregiver into a master nurse station computer of the nurse call equipment based on information communicated to the caregiver verbally by the patients.

5. The system of claim 1, wherein the information regarding the types of nurse calls placed by the patients is determined based on selections made by the patients on nurse call input devices of the nurse call equipment.

6. The system of claim 5, wherein the nurse call input devices comprises handheld pillow speaker units having a plurality of nurse call buttons, each nurse call button corresponding to a call type that is different than each of the other nurse call buttons.

7. The system of claim 5, wherein the nurse call input devices comprises a plurality of nurse call buttons provided on hospital beds located in the patient rooms, each nurse call button corresponding to a call type that is different than each of the other nurse call buttons.

8. The system of claim 1, wherein the notification comprises at least one of the following: (1) a message appearing on a wireless communication device carried by at least one caregiver (2) a message appearing on a status board display located in a caregiver work area, (3) a message appearing on a master nurse station computer of the nurse call system, or (4) illumination of at least one light of an indicator assembly located adjacent a door of at least one of the patient rooms.

9. The system of claim 1, wherein the notification comprises at least two of the following: (1) a message appearing on a wireless communication device carried by at least one caregiver (2) a message appearing on a status board display located in a caregiver work area, (3) a message appearing on a master nurse station computer of the nurse call system, or (4) illumination of at least one light of an indicator assembly located adjacent a door of at least one of the patient rooms.

10. The system of claim 1, wherein the notification comprises at least three of the following: (1) a message appearing on a wireless communication device carried by at least one caregiver (2) a message appearing on a status board display located in a caregiver work area, (3) a message appearing on a master nurse station computer of the nurse call system, or (4) illumination of at least one light of an indicator assembly located adjacent a door of at least one of the patient rooms.

11. The system of claim 1, wherein the notification comprises all of the following: (1) a message appearing on a wireless communication device carried by at least one caregiver (2) a message appearing on a status board display located in a caregiver work area, (3) a message appearing on a master nurse station computer of the nurse call system, or (4) illumination of at least one light of an indicator assembly located adjacent a door of at least one of the patient rooms.

12. The system of claim 1, wherein the first response time threshold and the second response time threshold are both established based on historical data from patient satisfaction surveys.

13. A system comprising
locating equipment to track the whereabouts of caregivers in a healthcare facility,
nurse call equipment to receive nurse call requests from patients located in patient rooms of the healthcare facility, the patient rooms being divided up into at least a first unit of the healthcare facility and a second unit of the healthcare facility, the nurse call equipment including at least one nurse call computer that keeps track of an amount of time it takes caregivers to respond to each nurse call and that keeps track of how long at least one caregiver is present in each patient room based on information received by the nurse call computer from the locating equipment, and
a patient experience module that receives information from the nurse call equipment regarding types of nurse calls placed by the patients, the types of nurse calls including a first call type and a second call type, the patient experience module comparing response times for each first call type to a first response time threshold for the first unit and comparing response times for each second call type to a second response time threshold for the first unit, the first response time threshold being a different amount of time than the second time threshold, the patient experience module initiating an alert to provide a notification that the first response time threshold or the second response time threshold has been exceeded for one or more of the first call types or the second call types of the first unit, respectively, and the patient experience module comparing response times for each first call type to a third response time threshold for the second unit and comparing response times for each second call type to a fourth response time threshold for the second unit, the third response time threshold being a different amount of time than the fourth time threshold, the patient experience module initiating an alert to provide a notification that the third response time threshold or the fourth response time threshold has been exceed for one or more of the first call types or the second call types of the second unit, respectively, wherein at least one of the first, second, third or fourth response time thresholds is established based on historical data from patient satisfaction surveys.

14. The system of claim 13, wherein the first response time threshold is a different amount of time than the third response time threshold.

15. The system of claim 13, wherein the second response time threshold is a different amount of time than the fourth response time threshold.

16. The system of claim 13, wherein the first unit comprises one of a maternity unit, a pediatrics unit, an intensive care unit, or a med/surg unit and wherein the second unit comprises a different one of the maternity unit, the pediatrics unit, the intensive care unit, or the med/surg unit than the first unit.

17. A system comprising
locating equipment to track the whereabouts of caregivers in a healthcare facility,
nurse call equipment to receive nurse call requests from patients located in patient rooms of the healthcare facility, the nurse call equipment including at least one nurse call computer that keeps track of the following key performance parameters: (1) a number of calls, (2) an amount of time it takes caregivers to respond to each nurse call, (3) a number of times at least one caregiver enters a patient room of a respective patient, and (4) how long at least one caregiver is present in each patient room, the key performance parameters being determined by the nurse call computer based on information received from other nurse call equipment and received from the locating equipment, and
a patient experience module that initiates an alert to provide a notification that any one or more of the key performance parameters exceeds a respective parameter threshold, wherein at least one of the parameter thresholds is determined based on historical data from patient satisfaction surveys.

18. The system of claim 17, wherein at least two of the parameter thresholds is determined based on historical data from patient satisfaction surveys.

19. The system of claim 17, wherein the key performance parameters further include one or more of the following: (5) a number of patient beds communicatively coupled to the nurse call equipment, (6) a number of patient beds having a bed exit system of the respective patient beds armed, or (7) a rounding compliance index.

* * * * *

UNITED STATES PATENT AND TRADEMARK OFFICE
CERTIFICATE OF CORRECTION

PATENT NO. : 10,068,461 B2
APPLICATION NO. : 15/461527
DATED : September 4, 2018
INVENTOR(S) : Timothy D. Wildman et al.

It is certified that error appears in the above-identified patent and that said Letters Patent is hereby corrected as shown below:

In the Claims

In Claim 8, Column 29, Line 20, please insert --,-- after --caregiver-- and before --(2)--.

In Claim 9, Column 29, Line 28, please insert --,-- after --caregiver-- and before --(2)--.

In Claim 10, Column 29, Line 36, please insert --,-- after --caregiver-- and before --(2)--.

In Claim 11, Column 29, Line 45, please insert --,-- after --caregiver-- and before --(2)--.

Signed and Sealed this
Twentieth Day of November, 2018

Andrei Iancu
*Director of the United States Patent and Trademark Office*